US011345946B2

(12) United States Patent
Opalsky et al.

(10) Patent No.: US 11,345,946 B2
(45) Date of Patent: May 31, 2022

(54) SYSTEMS AND METHODS FOR CAPACITIVE FLUID LEVEL DETECTION, AND HANDLING CONTAINERS

(71) Applicant: GEN-PROBE INCORPORATED, San Diego, CA (US)

(72) Inventors: David Opalsky, San Diego, CA (US); David Buse, San Diego, CA (US); James T. Tuggle, San Diego, CA (US); Alexander Navarro, San Diego, CA (US); Patrick Sheehan, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 485 days.

(21) Appl. No.: 15/934,339

(22) Filed: Mar. 23, 2018

(65) Prior Publication Data
US 2018/0282788 A1    Oct. 4, 2018

Related U.S. Application Data

(60) Provisional application No. 62/480,977, filed on Apr. 3, 2017, provisional application No. 62/476,529, filed on Mar. 24, 2017.

(51) Int. Cl.
*B01L 3/00*  (2006.01)
*C12Q 1/6806*  (2018.01)
(Continued)

(52) U.S. Cl.
CPC ............ *C12Q 1/6806* (2013.01); *B01L 3/565* (2013.01); *C12Q 1/686* (2013.01); *G01F 23/263* (2013.01);
(Continued)

(58) Field of Classification Search
CPC ....... C12Q 1/6806; C12Q 1/686; B01L 3/565; B01L 2200/026; B01L 2200/0689;
(Continued)

(56) References Cited

U.S. PATENT DOCUMENTS

2005/0013735 A1    1/2005  Gebrian et al.
2005/0052646 A1*   3/2005  Wohlstadter .............. B01L 9/56
                                                              356/311
(Continued)

FOREIGN PATENT DOCUMENTS

EP    0622796 A2    11/1994
EP    0819942 A2    1/1998
(Continued)

OTHER PUBLICATIONS

PCT, International Search Report and Written Opinion, International Patent Application No. PCT/US2018/024081, dated Oct. 2, 2018.
(Continued)

*Primary Examiner* — Benjamin R Whatley
(74) *Attorney, Agent, or Firm* — Sterne, Kessler, Goldstein & Fox P.L.L.C.; Charles B. Cappellari

(57) ABSTRACT

A fluid container holder includes a body having a receptacle configured to receive a container. The body has a conductive outer surface for connection to an electrical ground or voltage source, and the holder is not formed solely of an electrically conductive metal. A fluid container handling assembly includes a drawer having a holder supporting a fluid container, and a frame supporting the holder. The frame is movable between a first position providing access to the holder and a second position positioning the holder within the instrument. The assembly also includes a first lock securing the holder to the frame when the frame is at the first frame position and unlocking the holder from the frame
(Continued)

when the frame is at the second frame position. The assembly also includes a holder transporter configured to move the holder between a first holder position and a second holder position within the instrument.

14 Claims, 21 Drawing Sheets

(51) Int. Cl.
  *G01F 23/263* (2022.01)
  *G01N 35/04* (2006.01)
  *G01N 35/10* (2006.01)
  *C12Q 1/686* (2018.01)

(52) U.S. Cl.
  CPC ............ *G01F 23/268* (2013.01); *G01N 35/04* (2013.01); *G01N 35/1009* (2013.01); *B01L 2200/026* (2013.01); *B01L 2200/0689* (2013.01); *G01N 2035/0412* (2013.01); *G01N 2035/0425* (2013.01); *G01N 2035/0465* (2013.01); *G01N 2035/0498* (2013.01); *G01N 2035/1025* (2013.01); *G01N 2035/1048* (2013.01)

(58) Field of Classification Search
  CPC ..... G01F 23/263; G01F 23/268; G01N 35/04; G01N 35/1009; G01N 2035/0412; G01N 2035/0425; G01N 2035/0465; G01N 2035/0498; G01N 2035/1025; G01N 2035/1048
  See application file for complete search history.

(56) References Cited

U.S. PATENT DOCUMENTS

| | | | |
|---|---|---|---|
| 2008/0286158 A1* | 11/2008 | Watanabe | G01N 35/1009 422/400 |
| 2010/0034700 A1* | 2/2010 | Rousseau | B65D 71/50 422/400 |
| 2013/0027185 A1* | 1/2013 | Lavi | B01L 9/06 340/10.1 |
| 2013/0130369 A1* | 5/2013 | Wilson | G01N 35/1011 435/289.1 |
| 2014/0165645 A1* | 6/2014 | Schryver | B01L 7/00 62/457.1 |
| 2015/0292933 A1 | 10/2015 | Wiggli et al. | |
| 2016/0001292 A1* | 1/2016 | Motadel | B65D 25/108 206/563 |
| 2016/0060680 A1 | 3/2016 | Buse et al. | |
| 2016/0299167 A1* | 10/2016 | Sano | G01N 35/1016 |
| 2020/0105409 A1* | 4/2020 | Kochar | G06Q 10/10 |

FOREIGN PATENT DOCUMENTS

| | | |
|---|---|---|
| EP | 2148206 A1 | 1/2010 |
| JP | 60-59965 A | 4/1985 |
| JP | 62-289769 A | 12/1987 |
| JP | 09-127132 A | 5/1997 |
| JP | 10-038899 A | 2/1998 |
| JP | 2004-93518 A | 3/2004 |
| JP | 2008-309777 A | 12/2008 |
| JP | 2014-145661 A | 8/2014 |
| JP | 2015-203699 A | 11/2015 |

OTHER PUBLICATIONS

JPO Official Action, Japanese Patent Application No. 2019-551972, dated Feb. 22, 2022.

* cited by examiner

SYSTEMS AND METHODS FOR CAPACITIVE FLUID LEVEL DETECTION, AND HANDLING CONTAINERS

CROSS-REFERENCE TO RELATED APPLICATIONS

The present application claims the benefit of priority under 35 U.S.C. § 119(e) based on U.S. Provisional Application Ser. No. 62/480,977 filed on Apr. 3, 2017, and U.S. Provisional Application Ser. No. 62/476,529 filed on Mar. 24, 2017. The entire content of each of these applications is incorporated herein by reference thereto.

BACKGROUND

Field

This disclosure is directed to systems for detection of a fluid level through capacitive techniques and for handling containers, and related methods of use.

Background

Automated analytical procedures for analyzing a sample (e.g., a biological sample, chemical sample, etc.) typically require the use of consumable reagents in the form of fluid solutions and/or suspensions. In some cases, such consumables are stored in containers in an instrument that is configured to perform the analysis. During the analysis, these reagents may be accessed by a fluid transfer apparatus (e.g., a robotic pipettor) of the instrument through a penetrable seal, cover, or septum of the container. Over time, the reagents get consumed, and their levels in the containers decrease. Many techniques may be used to detect the level of the reagents in the containers. The current disclosure describes a capacitance based technique to detect the level of the reagent in the container.

Sometimes containers filled with fluid reagents are stored in and/or loaded into the instrument at different areas from where the fluid reagent is actually used by the instrument. The current disclosure describes various techniques for handling containers as the containers are loaded into and moved within the instrument.

SUMMARY OF THE DISCLOSURE

In some embodiments, a holder for supporting one or more containers of fluid is disclosed. The holder may include a bottom wall having an electrically conductive outer surface for connection to an electrical ground or voltage source, a top surface defining one or more openings, and one or more receptacles. Each receptacle of the one or more receptacles may depend from an opening of the one or more openings towards the bottom wall. Each receptacle is configured to receive at least one container of the one or more containers. The holder may not be formed solely of an electrically conductive material.

Additionally or alternatively, embodiments of the system may include one or more of the following features: the electrically conductive outer surface may be provided by an electrically conductive material affixed to an electrically nonconductive surface of the bottom wall; the electrically conductive material may be coated on the electrically nonconductive surface of the bottom wall; the electrically conductive material may include one of aluminum and copper; the holder may further include first and second side walls, wherein the one or more receptacles may be between the first and second side walls; at least one of the first and second side walls may include an electrically conductive outer surface contiguous with the electrically conductive outer surface of the bottom wall; the electrically conductive outer surface of at least one of the first and second side walls may be provided by an electrically conductive material affixed to an electrically nonconductive surface; the holder may further include an RFID tag affixed to a non-conductive surface of the holder; the one or more receptacles may include multiple receptacles; each receptacle of the one or more receptacles may extend from one of the one or more openings on the top surface to an inner surface of the bottom wall opposite the outer surface.

In some embodiments, a holder for supporting one or more containers of fluid is disclosed. The holder may include a bottom wall, first and second side walls, a top surface defining one or more openings, and one or more receptacles between the first and second side walls. Each receptacle of the one or more receptacles (a) may be in communication with an opening of the one or more openings, (b) may extend from the opening towards the first surface of the bottom wall, and (c) may be configured to receive at least one container of the one or more containers. At least one of the bottom wall, the first side wall, and the second side wall may have an electrically conductive layer affixed to an outer surface thereof. The electrically conductive layer may be for connection to an electrical ground or voltage source.

Additionally or alternatively, embodiments of the system may include one or more of the following features: the electrically conductive layer may be affixed to at least one of the bottom wall, the first side wall, and the second side wall; the electrically conductive layer may be coated on at least one of the bottom wall, the first side wall, and the second side wall; the electrically conductive layer may include one of aluminum and copper; the first and second side walls may be electrically nonconductive and extend between the top surface and the bottom wall; the bottom wall and at least one of the first and second side walls may include the electrically conductive layer; the electrically conductive layer may extend from the bottom wall to the top surface of at least one of the first and second side walls; the one or more receptacles may include multiple receptacles; each receptacle of the one or more receptacles may extend from one of the one or more openings on the top surface to the first surface of the bottom wall, and a base of a container positioned in each receptacle contacts the first surface.

In some embodiments, a frame for supporting one or more containers of fluid is disclosed. The frame may include one or more holders. Each holder of the one or more holders may include a top surface defining one or more openings, a bottom wall having an electrically conductive outer surface for connection to an electrical ground or voltage source, one or more receptacles, wherein each receptacle of the one or more receptacles may depend from an opening of the one or more openings towards the bottom wall, and one or more containers containing a fluid. Each container of the one or more containers may be (a) positioned in a receptacle of the one or more receptacles, and (b) may be configured to receive a probe tip of a fluid transfer device adapted for capacitive fluid level sensing.

Additionally or alternatively, embodiments of the system may include one or more of the following features: the electrically conductive outer surface may be affixed to an electrically nonconductive surface of the bottom wall; the electrically conductive outer surface may be coated on the electrically nonconductive surface of the bottom wall; the electrically conductive outer surface may include one of aluminum and copper; each holder may further include first and second side walls extending between the top surface and the bottom wall, wherein the one or more receptacles may be between the first and second side walls; at least one of the first and second side walls may include an electrically conductive outer surface contiguous with the electrically conductive outer surface of the bottom wall; the electrically conductive outer surface of at least one of the first and second side walls may be affixed to an electrically nonconductive surface; the electrically conductive outer surface of at least one of the first and second side walls is coated on the electrically nonconductive surface; the bottom wall, the first side wall, and the second side wall may be part of a single component made of an electrically nonconductive material; frame may further include a cover configured to retain a container in a receptacle; the cover may include an electrically nonconductive portion that extends over at least a portion of a top surface of the container; at least one of the one or more containers may include an electrically conductive seal that the probe tip of fluid transfer device passes through when the probe tip of fluid transfer device enters the container; the one or more holders may be positioned on, or proximate to, a surface of the frame such that the electrically conductive outer surface of a first holder of the one or more holders is electrically grounded by a direct or indirect physical contact with the surface; the frame may further include an electrically conductive spring positioned between the electrically conductive outer surface of the first holder and the surface of the frame to establish the physical contact; the one or more holders may include multiple holders, and the one or more receptacles may include multiple receptacles; the frame may further include one or more indicators configured to indicate a status of the one or more containers; the one or more holders may be removably positioned on the frame.

In some embodiments, an instrument configured to analyze one or more samples is disclosed. The instrument may include one or more holders for supporting one or more containers of fluid. Each holder may include a top surface defining one or more openings, first and second side walls, and a bottom wall having an electrically conductive outer surface configured to be connected to an electrical ground. The holder may also include one or more receptacles between the first and second side walls. Each receptacle of the one or more receptacles may depend from an opening of the one or more openings towards the bottom wall, and each receptacle may also be configured to receive at least one container of the one or more containers, and a probe tip of the fluid transfer device adapted for capacitive fluid level sensing. The one or more containers may be accessible by the probe tip of the fluid transfer device.

Additionally or alternatively, embodiments of the system may include one or more of the following features: the electrically conductive outer surface may be affixed to an electrically nonconductive surface of the bottom wall; the electrically conductive outer surface may be coated on an electrically nonconductive surface of the bottom wall; the electrically conductive outer surface may include one of aluminum and copper; at least one of the first and second side walls may include an electrically conductive outer surface contiguous with the electrically conductive outer surface of the bottom wall; the electrically conductive surface of the at least one of the first and second side walls may be affixed to an electrically nonconductive surface; the electrically conductive outer surface of the at least one of the first and second walls may be coated on the electrically nonconductive surface; the instrument may further include an electrically conductive brush configured to contact at least one of the bottom wall and the at least one of the first and second side walls to electrically ground the electrically conductive outer surface of at least one of the bottom wall and the at least one of the first and second side walls; the instrument may further include a transporter configured to move at least one holder of the one or more holders from a first location to a second location in the instrument, wherein the second location includes the electrically conductive brush; the one or more holders may be positioned on, or proximate to, a surface of the instrument such that the electrically conductive outer surface of a first holder of the one or more holders is electrically grounded by a direct or indirect physical contact with the surface; the instrument may further include a spring positioned between the electrically conductive outer surface of the first holder and the surface of the instrument to establish the physical contact; each holder includes at least one container of the one or more containers may be positioned in at least one of the one or more receptacles; each holder may further include a cover configured to retain the one or more containers in the holder while providing access to the one or more containers by the probe tip of the fluid transfer device, the cover may include an electrically nonconductive portion that extends at least partially over the one or more containers; the one or more holders may include multiple holders removably positioned on the instrument, and the one or more receptacles may include multiple receptacles.

In some embodiments, a method of detecting a fluid level in a container including a fluid is disclosed. The method may include positioning the container in a receptacle of a holder such that a bottom surface of the container is disposed on, or is positioned proximate to, a first surface of the holder, wherein a second surface of the holder opposite the first surface includes an electrically conductive layer that is electrically grounded. The method may also include inserting a probe tip of the fluid transfer device having a probe tip configured for capacitive fluid level sensing into the container to detect a level of the fluid in the container.

Additionally or alternatively, embodiments of the system may include one or more of the following features: the electrically conductive layer may be attached to an electrically nonconductive surface of the holder; the electrically conductive layer may be coated on an electrically nonconductive surface of the holder; the holder may include a top surface spaced apart from the first surface such that the receptacle extends from the top surface towards the first surface, and the holder may further include a side wall having an electrically conductive side surface extending from the electrically conductive layer of the second surface towards the top surface; the method may further include electrically grounding the electrically conductive layer of the second surface by contacting the electrically conductive side surface to an electrical ground via an electrically conductive brush; contacting the electrically conductive side surface to an electrical ground may include moving the holder from a first location to a second location to engage the electrically conductive side surface with the electrically conductive brush; the electrically conductive layer of the second surface may be connected to an electrical ground via an electrically conductive metal spring; a top surface of the container opposite the bottom surface of the container may include an electrically conductive seal, wherein inserting the probe tip of the fluid transfer device may include inserting the probe tip into the container through the electrically conductive seal; the method may further include retracting the probe tip of the fluid transfer device from the container; retracting the probe tip of the fluid transfer device from the container may include restraining the container in the receptacle using a cover that extends over at least a portion of the container, wherein the cover includes an electrically nonconductive surface facing the electrically conductive seal.

In some embodiments, a method of extracting fluid from a container is disclosed. The method may include positioning the container in a receptacle of a holder. The receptacle may extend from a top surface of the holder towards a bottom wall of the holder, the bottom wall including an electrically conductive bottom surface that is connected to an electrical ground. The method may also include inserting a probe tip of the fluid transfer device having a probe tip configured for capacitive fluid level sensing into the container, detecting a level of the fluid in the container using the probe tip, and extracting fluid from the container using the probe tip of the fluid transfer device.

Additionally or alternatively, embodiments of the system may include one or more of the following features: the electrically conductive bottom surface may be affixed to an electrically nonconductive surface of the holder; the electrically conductive bottom surface may be coated on the electrically nonconductive surface of the holder; the holder may include a side wall that extends from the bottom wall to the top surface, the side wall may include an electrically conductive side surface that is contiguous with the electrically conductive bottom surface of the bottom wall; the method may further include electrically grounding the electrically conductive surfaces of the holder by contacting the bottom surface or the side surface to an electrical ground or voltage source via an electrically conductive brush; contacting the side surface to an electrical ground may include moving the holder from a first location to a second location to contact the side surface with the electrically conductive brush; the bottom surface may be connected to electrical ground via an electrically conductive spring; a top surface of the container opposite the bottom wall may include an electrically conductive seal, and wherein inserting the fluid transfer device may include inserting the probe tip into the container through the electrically conductive seal; the method may further include retracting the fluid transfer device from the container, and restraining the container in the receptacle using a cover that extends over at least a portion of the container.

In some embodiments, an assembly for handling a fluid container within an instrument includes a drawer having a holder, a frame, and a first lock. The holder is configured to support at least one fluid container. The frame is configured to support the holder, and is movable between (a) a first frame position providing access to the holder and (b) a second frame position positioning the holder within the instrument at a first holder position. The first lock secures the holder to the frame when the frame is at the first frame position and unlocks the holder from the frame when the frame is at the second frame position. The assembly also includes a holder transporter configured to move the holder between (a) the first holder position and (b) a second holder position within the instrument, wherein at least a portion of a path that the holder travels between the first holder position and the second holder position comprises a vertical component.

In some embodiments, the holder includes a first knob, and the frame comprises a base panel defining a first opening. The first knob of the holder extends through the opening when the holder is supported by the frame. The first lock can include an arm movable relative to the opening between (a) a first arm position at which the arm engages a portion of the first knob extending through the opening, thereby securing the holder to the frame, and (b) a second arm position at which the arm is disengaged from the portion of the first knob extending through the opening, thereby unlocking the holder from the frame. The holder can also include a second knob, and the base panel of the frame can further define a second opening. The second knob of the holder extends through the second opening when the holder is supported by the frame. The first lock, at the first arm position, engages a portion of the second knob extending through the second opening and, at the second arm position, is disengaged from the portion of the second knob extending through the second opening, thereby unlocking the holder from the frame.

In some embodiments, the arm comprises a first hook configured to engage the portion of the first knob extending through the first opening, and a second hook configured to engage the portion of the second knob extending through the second opening. The first knob and the second knob can each comprise a flange extending from a distal end of the respective first knob and second knob. The first hook and the second hook, at the first arm position, can be positioned between the respective flange and the base panel of the frame, thereby inhibiting vertical movement of the holder relative to the frame. In some embodiments, the arm rotates about an axis defined by a pivot pin coupled to the frame. The arm can be biased to the first arm position or to the second arm position. The drawer further includes a spring that biases the arm.

In some embodiments, the holder defines at least one slot, and the frame comprises at least one holder engagement member configured to be received in the at least one slot when the holder is supported by the frame. The at least one holder engagement member can be a protrusion extending from a panel.

In some embodiments, the drawer further comprises a stationary support, and the frame is movable relative to the stationary support. The drawer also includes a second lock configured to inhibit movement of the frame relative to the stationary support when the frame is at the second frame position and the holder is unlocked from the frame. The second lock can include one of a hook and a catch coupled to the moveable frame, and the other of the hook and the catch coupled to the stationary support. The hook cooperatively engages the catch when the frame is at the second frame position.

In some embodiments, the holder transporter includes a holder support configured to cooperatively engage the holder at the first holder position when the frame is at the second frame position. The holder support can include a pin, and the holder can include a channel configured to receive the pin when the moveable frame is at the second frame position, thereby generating an interference fit between the pin and the holder. The holder can also include a spring arm defining, at least in part, the channel. The holder can also include a flange, and the holder support can include a surface supporting the flange when the frame is at the second frame position. The holder support can also include a top portion spaced apart from the surface and inhibiting upward movement of the at least one fluid container supported by the holder when the frame is at the second frame position. The top portion may define an opening exposing at least a portion of the at least one fluid container supported by the holder when the moveable frame is at the second frame position.

In some embodiments, the holder transporter includes an actuator, and a movable transporter arm coupling the actuator to the holder support. The actuator rotates the movable transporter arm such that the holder support moves the holder along an arcuate path between the first holder position and the second holder position. The actuator can be an electric motor. The transporter can also include a second movable transporter arm coupled to the holder support.

In some embodiments, the instrument is an analytical instrument. The analytical instrument can include a first module configured to perform first analyses on samples, and a second module configured to perform second analyses different from the first analyses. The first holder position is within the first module, and the second holder position is within the second module. The first analyses can include performing first nucleic acid amplification reactions requiring thermal cycling, and the second analyses can include performing second nucleic acid amplification reactions requiring isothermal conditions. The first nucleic acid amplification reactions can include PCR reactions, and the second nucleic acid amplification reactions can include TMA reactions, NASBA reactions, and/or SDA reactions.

In some embodiments, a transporter moves a holder within an instrument. The holder is configured to support a container. The transporter can include a holder support configured to releasably couple with the holder, and an actuator coupled to the holder support and configured to move the holder support. The holder support is movable between (a) a first position at which the holder support is configured to receive the holder and (b) a second position. At least a portion of a path that the holder support travels between the first position and the second position comprises a vertical component.

In some embodiments, the holder support includes a pin configured to be received in a channel defined by the holder, thereby generating an interference fit between the pin and the holder. In some embodiments, the holder support includes a surface configured to support a portion of the holder, and a top portion spaced apart from the surface configured to inhibit upward movement of a fluid container supported by the holder when the holder is coupled to the holder support. The top portion may define an opening exposing at least a portion of the fluid container supported by the holder.

In some embodiments, the actuator comprises an electric motor.

In some embodiments, the transporter also includes a movable arm coupling the actuator to the holder support. The actuator can rotate the movable arm such that the holder support moves along an arcuate path.

The transporter can be part of an analytical instrument. The analytical instrument can include a first module configured to perform first analyses on samples, and a second module configured to perform second analyses different from the first analyses. The first position is within the first module, and the second position is within the second module, in some embodiments.

In some embodiments, wherein the first analyses comprise performing first nucleic acid amplification reactions requiring thermal cycling, and the second analyses comprise performing second nucleic acid amplification reactions requiring isothermal conditions. The first nucleic acid amplification reactions can include performing PCR reactions, and the second nucleic acid amplification reactions can include performing TMA reactions, NASBA reactions, and/or SDA reactions.

In some embodiments, a method of handling a fluid container used by an instrument includes (a) moving a frame supporting a holder from (i) a first frame position providing access to the holder to (ii) a second frame position positioning the holder within the instrument, the holder supporting at least one fluid container; (b) unlocking the holder from the frame; and (c) moving, after step (b), the holder from the frame to another position along a path comprising a vertical component.

In some embodiments, step (b) includes moving a locking arm from (i) a first lock position at which the locking arm engages a portion of a first knob of the holder to (ii) a second lock position at which the arm is disengaged from the portion of the first knob of the holder. The locking arm can engage a portion of a second knob of the holder at the first lock position, and the locking arm can be disengaged from the portion of the second knob of the holder at the second lock position.

In some embodiments, step (b) can occur after or concurrently with step (a).

In some embodiments, the method also includes (d) engaging the holder with a holder support of the holder transporter when the frame is at the second frame position. Step (d) can occur after or concurrently with step (a).

In some embodiments, step (c) includes rotating an arm coupled to the holder support using an actuator, thereby moving the holder support along an arcuate path.

In some embodiments, the frame is positioned within a first module of an analytical instrument configured to perform first analyses on samples, and the other position the holder is moved to along the path is in a second module of the analytical instrument configured to perform second analyses on samples different than the first analyses. The first analyses can include performing first nucleic acid amplification reactions requiring thermal cycling, and the second analyses can include performing second nucleic acid amplification reactions requiring isothermal conditions for the duration of the second nucleic acid amplification reactions. The first nucleic acid amplification reactions can include PCR reactions, and the second nucleic acid amplification reactions can include TMA reactions, NASBA reactions, or SDA reactions.

In some embodiments, after step (c), the method further includes (e) inserting a probe tip of a first fluid transfer device into the fluid container at the other position in the second module of the analytical instrument; (f) aspirating at least a portion of fluid in the fluid container using the first fluid transfer device; and (g) withdrawing the probe tip of the first fluid transfer device from the fluid container.

In some embodiments, the method further includes (h) inserting a probe tip of a second fluid transfer device into the fluid container supported by the frame when the frame is at the second frame position; (i) aspirating at least a portion of fluid in the fluid container using the second fluid transfer device; and (j) withdrawing the probe tip of the second fluid transfer device from the fluid container. In some embodiments, steps (h), (i), and (j) occur before step (c).

In some embodiments, the method includes (k) moving the holder from the other position in the second module of the analytical instrument to the frame in the first module. The method can also include (l) moving the frame supporting the holder from (i) the second frame position to (ii) the first frame position; and (m) locking the holder to the frame. In some embodiments, step (m) occurs before or concurrently with step (l).

In some embodiments, the method further includes manually removing the fluid container from the holder while the frame is at the first frame position and the holder is locked to the frame.

Further features and advantages of the embodiments, as well as the structure and operational of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE FIGURES

The accompanying drawings, which are incorporated in and constitute a part of this specification, illustrate various examples and together with the description, serve to explain the principles of the disclosed examples.

The features and advantages of the embodiments will become more apparent from the detailed description set forth below when taken in conjunction with the drawings, in which like reference characters identify corresponding elements throughout.

DETAILED DESCRIPTION

Figure 1A:
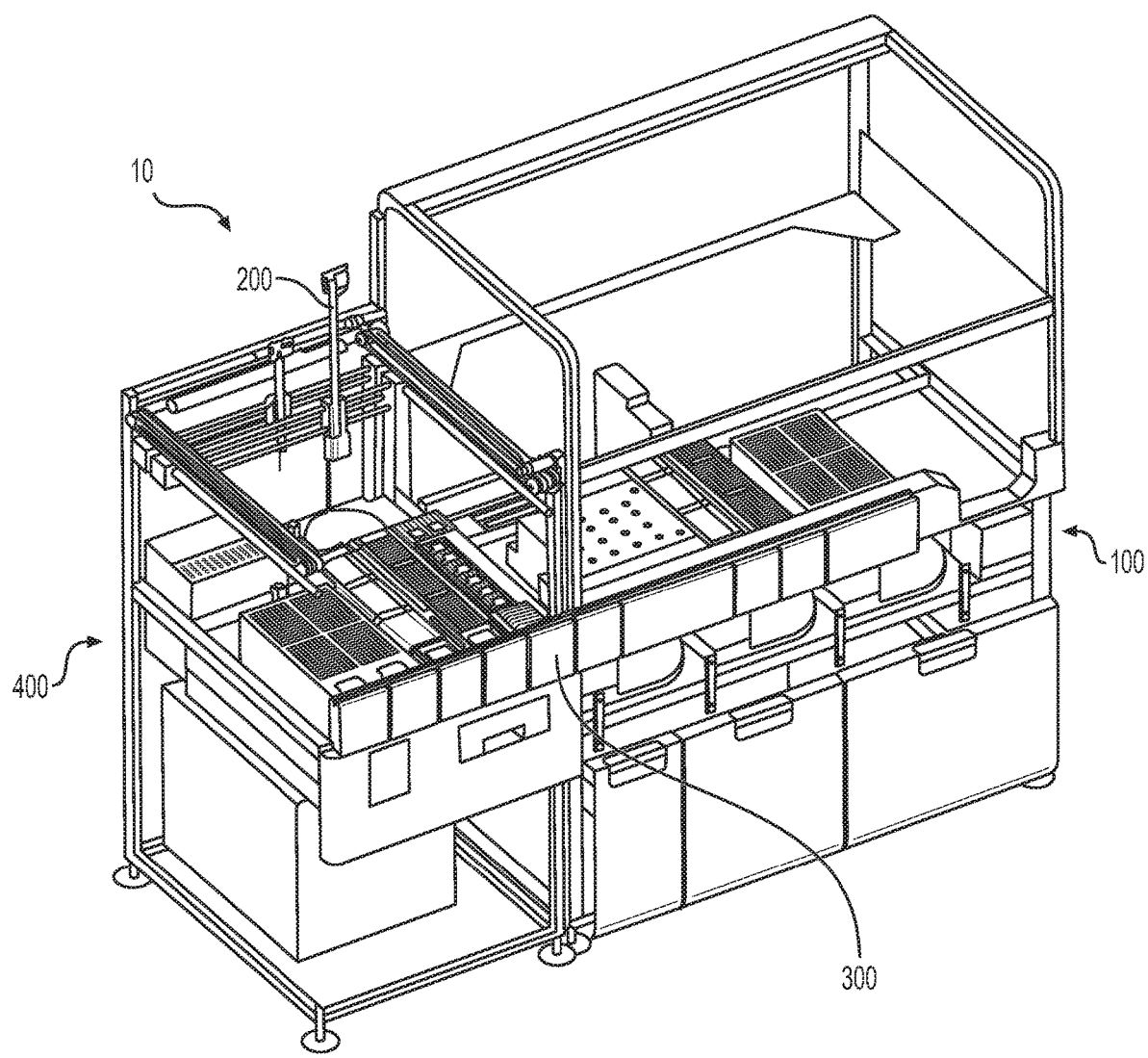
FIG. 1A is a perspective view of an exemplary diagnostic system comprising a first module and a second module, according to an embodiment.

Reference will now be made in detail to examples of the present disclosure, which are illustrated in the accompanying drawings. Wherever possible, the same reference numbers will be used throughout the drawings to refer to the same or like parts. Although embodiments of the current disclosure are described with reference to its application in an instrument that performs molecular genetics related analysis, this is only exemplary. As a person skilled in the art would recognize, embodiments of the current disclosure may be applied to any application.

Unless defined otherwise, all terms of art, notations and other scientific terms/terminology used herein have the same meaning as is commonly understood by one of ordinary skill in the art to which this disclosure belongs. All patents, applications, published applications and other publications (literature) referred to herein are incorporated by reference in their entirety. If a definition set forth in this section is contrary to or otherwise inconsistent with a definition set forth in the literature incorporated herein by reference, the definition set forth in this section prevails over the definition that is incorporated by reference.

References in the specification to "one embodiment," "an embodiment," a "further embodiment," "an example embodiment," "some aspects," "a further aspect," "aspects," "for example," "exemplary," "some embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, such feature, structure, or characteristic is also a description in connection with other embodiments whether or not explicitly described. Further, as used herein, "a" or "an" means "at least one" or "one or more."

In the discussion that follows, relative terms such as "about," "substantially," "approximately," etc. are used to indicate a possible variation of ±10% in a stated numeric value. Further, the description below may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, inside, outside, inner, outer, proximal, distal, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

As used herein, a "sample" refers to any material to be analyzed, regardless of the source. The material can be in its native form or any stage of processing (e.g., the material can be chemically altered or it can be one or more components of a sample that have been separated and/or purified from one or more other components of the sample). A sample can be obtained from any source, including, but not limited to, an animal, environmental, food, industrial or water source. Animal samples include, but are not limited to, peripheral blood, plasma, serum, bone marrow, urine, bile, mucus, phlegm, saliva, cerebrospinal fluid, stool, biopsy tissue including lymph nodes, respiratory tissue or exudates, gastrointestinal tissue, cervical swab samples, semen or other body or cellular fluids, tissues, or secretions. Samples can be diluted or contained within a receptacle containing diluents, transport media, preservative solution, or other fluids. As such, the term "sample" is intended to encompass samples contained within a diluent, transport media, and/or preservative or other fluid intended to hold a sample.

As used herein, a "diagnostic instrument" refers to any instrument capable of performing an assay on a sample and rendering a result. For example, a diagnostic instrument includes any instrument capable performing an assay on a sample to determine the presence or amount of an analyte in the sample. Any instrument capable of performing a hybridization assay, a molecular assay including a nucleic-acid-based amplification reaction, a sequencing assay, an immunoassay, or chemical assay on a sample is included in this definition of a diagnostic instrument. Exemplary diagnostic instruments capable performing an assay on a sample to determine the presence of an analyte in the sample include the Tigris®, Panther®, and Panther Fusion® systems sold by Hologic, Inc., Marlborough, Mass., as well as any of the diagnostic instruments disclosed in U.S. Patent Application Publication No. 2016/0060680, published Mar. 3, 2016.

FIG. 1A illustrates an exemplary analysis or diagnostic instrument or system 10 used to describe embodiments of the current disclosure. Diagnostic system 10 illustrated in FIG. 1A is a Panther Fusion system (from Hologic, Inc.) configured to perform molecular testing of multiple samples. However, this system 10 is only exemplary, and embodiments of the current disclosure may be used in any application and with any (or no) instrument. Diagnostic system 10 may be configured to perform any type of analysis of a sample. In some embodiments, the diagnostic system may be configured to perform a plurality of different analyses (e.g., molecular assays) on a plurality of samples. In some embodiments, diagnostic system 10 may be configured to perform different target nucleic acid amplification reactions on different samples. For example, a plurality of samples may be loaded on, or in, diagnostic system 10, and system 10 may perform a first analysis (e.g., a first target nucleic acid amplification reaction) on a first subset of a plurality of samples, and perform a different analysis (e.g., a second target nucleic acid amplification reaction) on a second subset of the plurality of samples.

In some embodiments, diagnostic system 10 may have a modular structure and may be comprised of multiple modules operatively coupled together. For example, system 10 may comprise a first module 100 and a second module 400 operatively coupled together. Both first module 100 and second module 400 may be configured to perform one or more steps of the first analysis and/or the second analysis. In some embodiments, first and second modules 100, 400 may be separate modules selectively coupled together. That is, first module 100 can be selectively and operatively coupled to one second module 400, and first module 100 can be selectively decoupled from this second module 400 and coupled to a different second module 400. First and second modules 100, 400 may be coupled together by any method. For example, fasteners (for example, bolts or screws), clamps, belts, straps, or any combination of fastening/attachment devices may be used to couple these modules together. In some embodiments, diagnostic system 10 may be an integral, self-contained structure (that is, first module 100 cannot be coupled to and decoupled from second module 400).

In some embodiments, power, data, and/or utility lines or conduits (air, water, vacuum, etc.) may extend between first and the second modules 100, 400. In some embodiments, first module 100 is configured to perform first nucleic acid amplification reactions requiring isothermal conditions, i.e., substantially constant temperature, during the duration of the first nucleic acid amplification reactions (e.g., transcription-mediated amplification reactions (TMA), nucleic acid sequence based amplification (NASBA) reactions, and strand displacement amplification (SDA) reactions), and second module 400 is configured to perform second nucleic acid amplification reactions requiring thermal cycling (e.g., polymerase chain reactions (PCR)). In some embodiments, first module 100 may be a diagnostic system that was previously purchased by a customer, and second module 400 may be a later purchased diagnostic module that expands the analysis capabilities of the combined system. For example, in an embodiment where system 10 is a Panther Fusion® system (from Hologic, Inc.), first module 100 may be a Panther® instrument configured to perform TMA assays of samples, and module 400 may be a Panther Fusion® Sidecar that is configure to extend the functionality of the Panther instrument by adding PCR assay capabilities.

An exemplary diagnostic system 10 with exemplary first and second modules 100, 400 is described in U.S. Patent Publication Numbers 2016/0060680 and 2016/0032358 which are incorporated by reference herein in their entireties. Exemplary systems, functions, components, and capabilities of first and second modules 100, 400 are described in the above-referenced publications and are not described herein for the sake of brevity. Among other components, first and/or second modules 100, 400 may include compartments (e.g., drawers, cabinets, etc.) that may be opened and loaded with containers holding samples, containers storing reagents, receptacles for performing reactions involved in the analysis, etc. These compartments include a fluid drawer 300 that stores a plurality of containers with reagents that are used in the analysis. The components of first and/or second modules 100, 400 also include container, receptacle, or holder transporters for moving containers, receptacles, or holders between different load stations (heaters, incubators, etc.) of modules 100, 400, and fluid transfer devices that transfer desired amounts of samples and reagents from the containers into the receptacles. These substance transfer devices may include robotic pipettors 200 configured for controlled, automated movement, between different locations (e.g., fluid drawer 300, sample containers, reaction receptacles, etc.) of modules 100, 400. Robotic pipettors 200 include probes with tips (e.g., disposable tips) that are configured to access the containers holding the samples and the reagents and transfer desired amounts of their contents to reaction receptacles and vials.

In one exemplary embodiment, fluid drawer 300 is configured to hold a plurality of reagent containers. In some embodiments, fluid drawer 300 may be a part of second module 400. However, it is also contemplated that fluid drawer 300 is a part of first module 100.

Figure 1B:
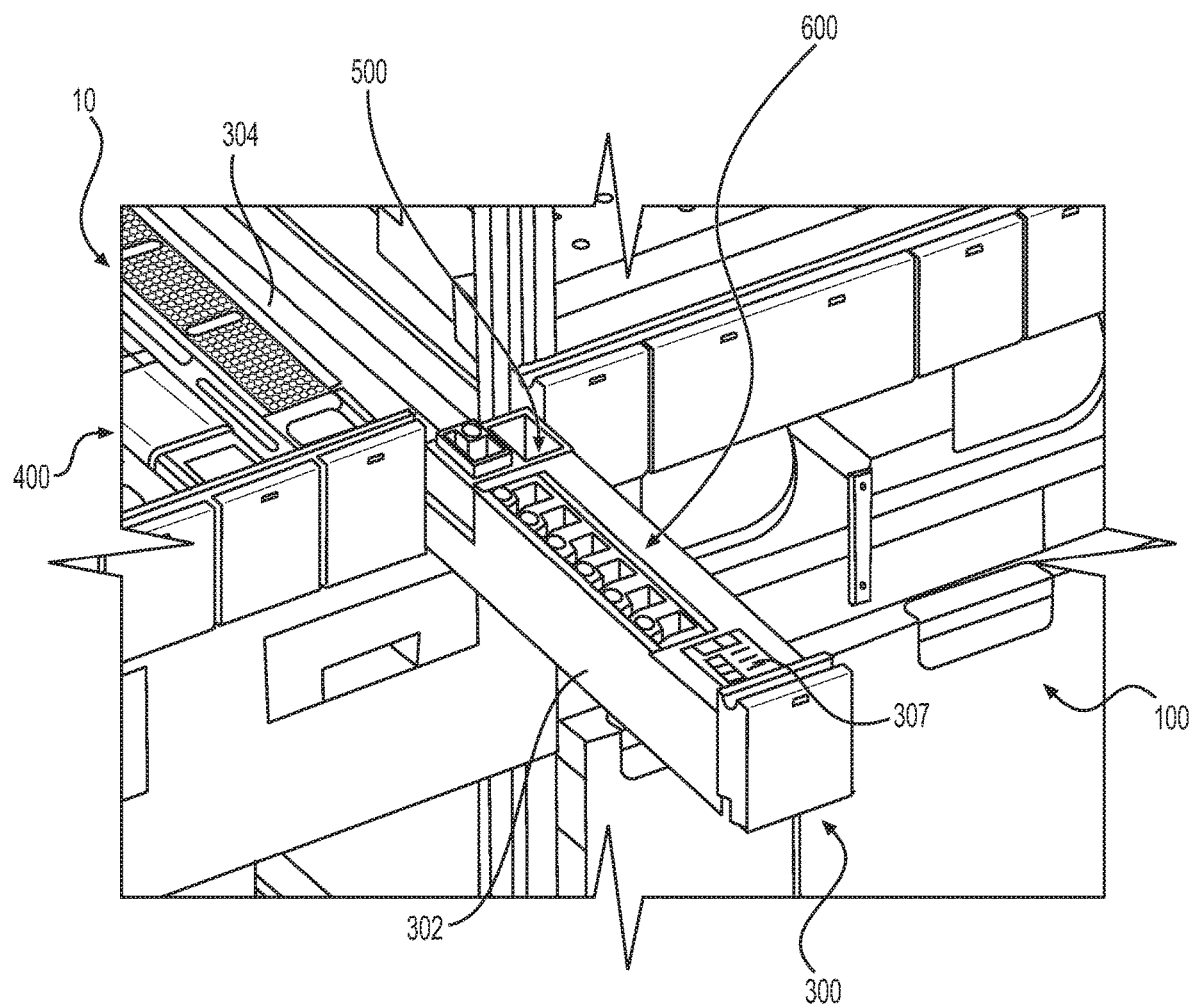
FIG. 1B is an enlarged view of a portion of the diagnostic system of FIG. 1A with a fluid drawer in an opened positioned, according to an embodiment.
Figure 2:
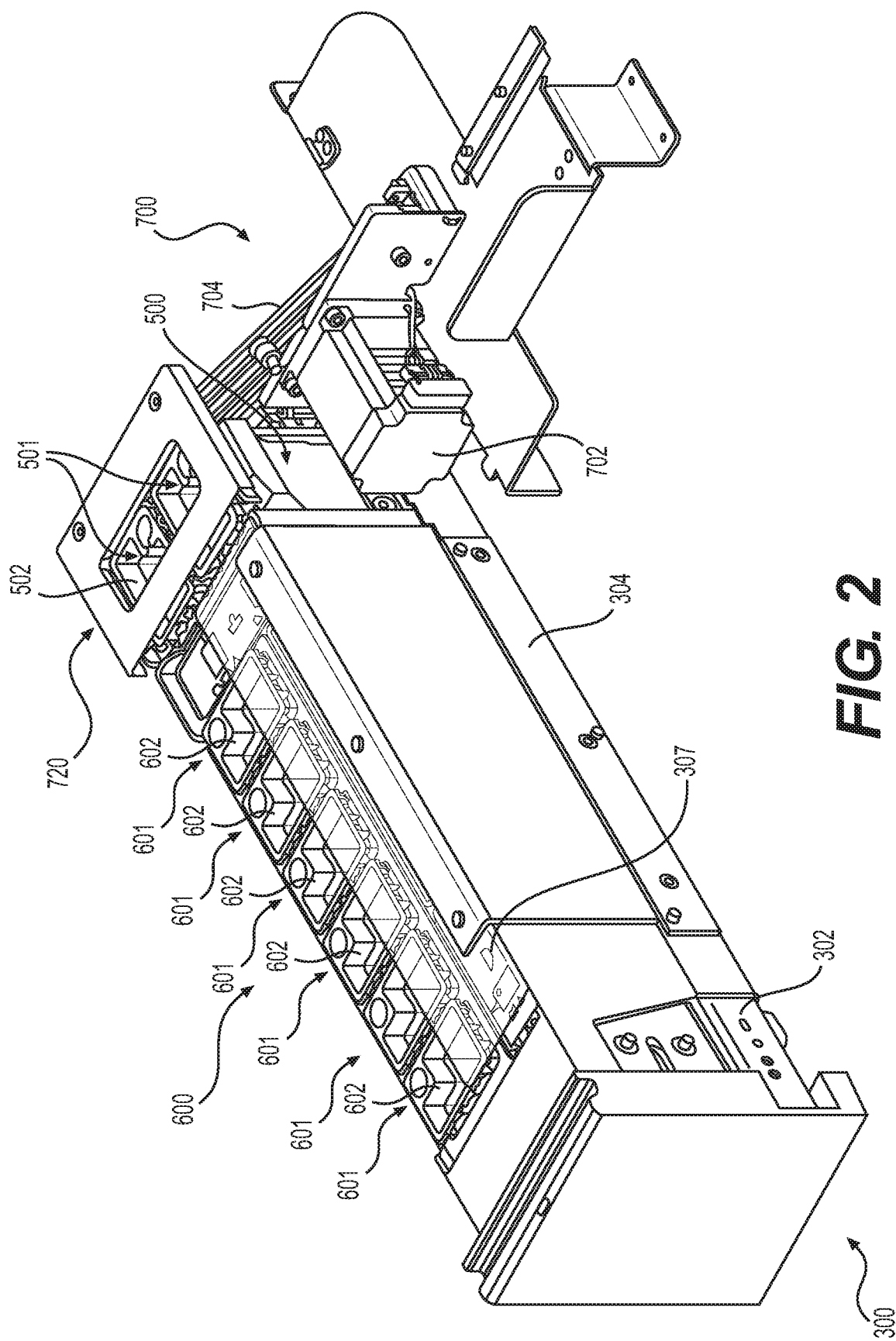
FIG. 2 is an exemplary fluid drawer of the system of FIG. 1A in a closed position, according to an embodiment.

Fluid drawer 300 can include a movable frame 302 and a stationary support 304. Movable frame 302 can be movably coupled (for example, slidably) to stationary support 304 such that frame 302 can move relative to stationary support 304. Stationary support 304 can be integral with the frame of system 10 or coupled to the frame of system 10. Frame 302 can move between a closed position in which frame 302 and the components coupled there to or supported thereby are within instrument 10 (as shown in FIGS. 1A and 2), and an opened position in which the components coupled there to or supported thereby are accessible to an operator (as shown in FIG. 1B). For example, a door or cover panel of fluid drawer 300 (or the housing of second module 400) can grabbed by an operator to slide frame 302 out from the closed position within instrument 10 to the opened position, thereby providing the operator access to the contents of fluid drawer 300. The door or cover panel may provide an esthetically pleasing appearance to the front of second module 400. Automated locks, controlled by the system controller, may be provided to prevent frame 302 of fluid drawer 300 from being pulled open when second module 400 is operating. In some embodiments, visible and/or audible warning signals may be provided to indicate that fluid drawer 300 is not closed properly.

FIG. 1B is an enlarged perspective view of a portion of diagnostic system 10 with frame 302 of fluid drawer 300 at the opened position, according to an embodiment. And FIG. 2 is a perspective view of an exemplary fluid drawer 300 at the closed position and separated from the remainder of system 10. In the discussion below, reference will be made to both FIGS. 1B and 2. Fluid drawer 300 may include a frame 302 that may be slid out from stationary support 304, which is coupled to or integral with the main body of diagnostic system 10. Frame 302 of fluid drawer 300 may be opened by an operator to load containers carrying fluid reagents (i.e., any fluid used during an analysis performed by instrument 10) therein. Frame 302 of fluid drawer 300 may include one or more container-holders that are configured to hold one or more containers carrying the different types of reagents. In general, a container-holder may be a component that includes one or more receptacles (e.g., recesses, pockets, cavities, etc.) coupled to or formed thereon to receive a fluid filled container therein. In some embodiments, a container-holder may be a component molded using a nonconductive plastic or polymeric material. However, it is also contemplated that in some embodiments, container-holders may be formed using conductive materials, or different regions of a container-holder may be formed from different materials (e.g., nonconductive and conductive materials). In some exemplary embodiments, frame 302 of fluid drawer 300 includes a container-holder 500, which in some embodiments contains elution buffer containers or containers having any other desired reagent, and a container-holder 600, which in some embodiments contains non-elution buffer reagents or any other desired reagent. In some embodiments, at least container-holder 500 is removably coupled to frame 302. For example, container-holder 500 can move with frame 302 between the closed and opened positions, and then be removed or decoupled from frame 302 at the closed position (as described further below).

Figure 3:
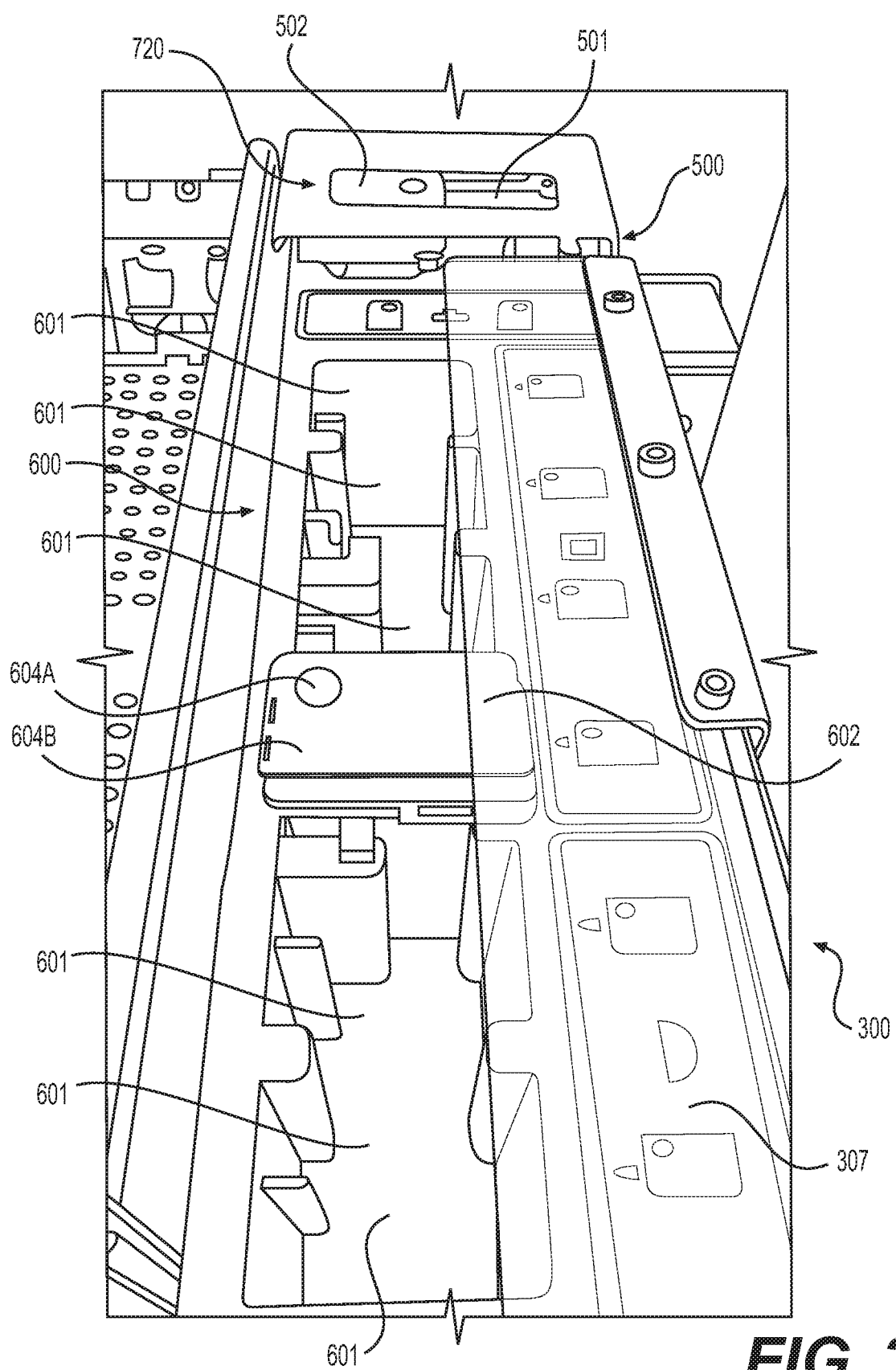
FIG. 3 illustrates exemplary container-holders in the fluid drawer of the system of FIG. 1A, according to an embodiment.

Although not a requirement, in some embodiments, container-holder 500 may include two receptacles 501, each configured to receive a container 502 (e.g., a container that contains an elution buffer) therein. For example, FIG. 2 illustrates an exemplary container-holder 500 including a container 502 in each of its two receptacles 501, and FIG. 3 illustrates an exemplary container-holder 500 including a container 502 in one of its two receptacles 501. And in some embodiments, container-holder 600 may include six receptacles 601, each configured to receive a reagent containing container therein. In some embodiments, the six receptacles of the reagent container-holder 600 may be configured to receive two oil containers and four reconstitution fluid containers 602 (see FIG. 3). For example, FIG. 2 illustrates an exemplary reagent container-holder 600 with a reagent container 602 in each receptacle 601, and FIG. 3 illustrates an exemplary reagent container-holder 600 with a reagent container 602 (for example, a reconstitution fluid container) in one of its six receptacles 601.

Figure 9:
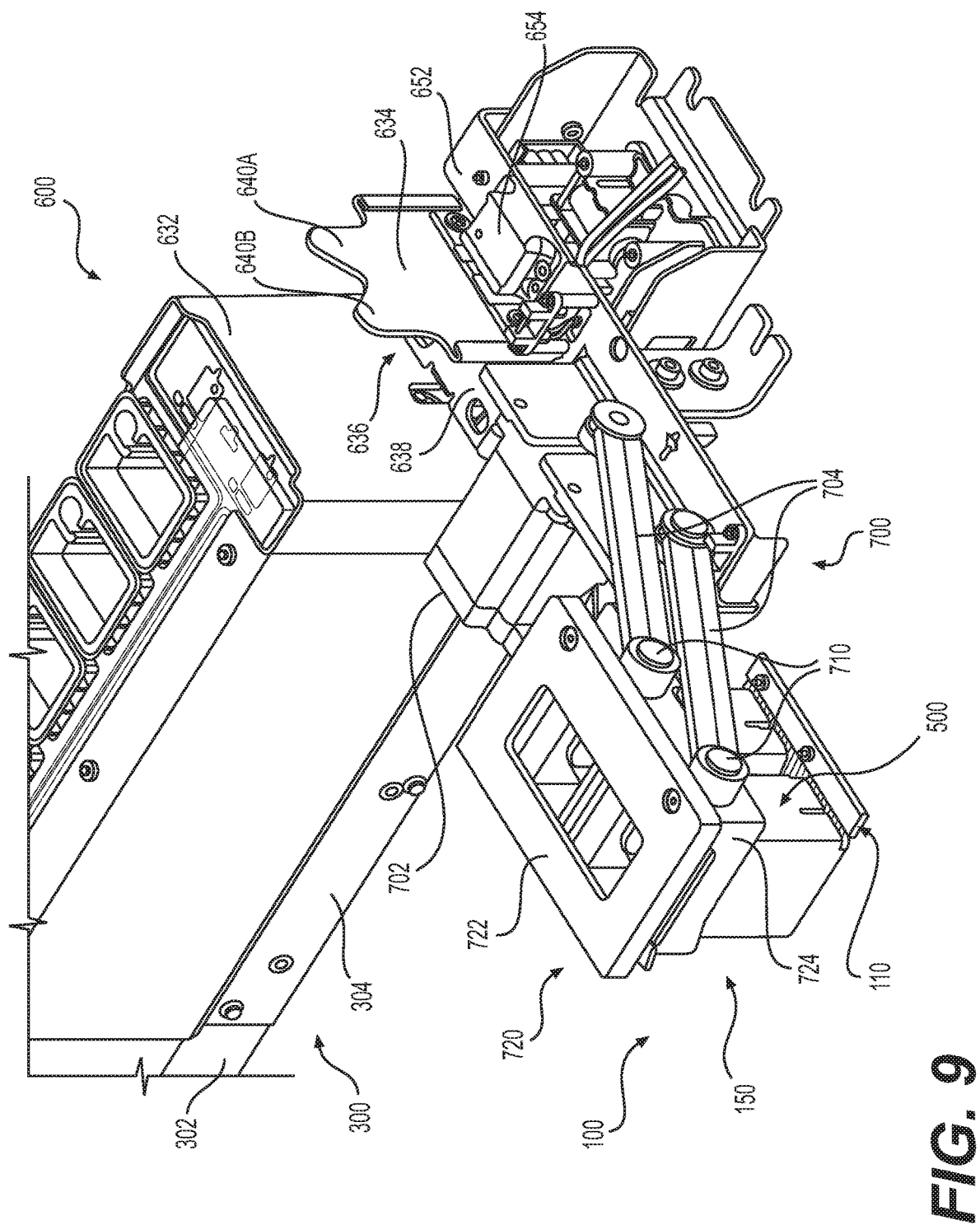
FIG. 9 is a rear perspective view of a fluid drawer and a holder transporter, according to an embodiment.

In some embodiments, container-holder 500 and container-holder 600 may be separate components that are placed adjacent to, or spaced apart from, each other. For example, in some embodiments, container-holder 500 may fit in a region (e.g., any pocket, cavity, recess, etc.) of frame 302. As best seen in FIG. 9, for example, a recess 636 configured to receive container-holder 500 is defined in frame 302. Recess 636 can be defined, at least in part, by a panel 632 of container-holder 600, a base panel 638 of frame 302, and a back panel 634 of frame 302. As such, each of panel 632, base panel 638, and back panel 634 (and recess 636 defined thereby) move as frame 302 moves between the opened and closed positions. As best seen in FIG. 9, a side of recess 636 that intersects the path container-holder 500 travels is substantially unbounded (unlike the front, bottom, and back sides of recess 636), allowing container-holder 500 to be easily inserted within recess 636 by transporter 700.

Although a fluid drawer 300 with two separate container-holders (container-holder 500 and container-holder 600) is described above, this is only exemplary. In general, fluid drawer 300 may include any number of container-holders, each having any number of receptacles. For instance, in some embodiments, instead of two container-holders (e.g., container-holder 500 with two receptacles 501 and a container-holder 600 with six receptacles 601), a single container-holder (e.g., with eight receptacles) may be provided in fluid drawer 300. The number and size of the receptacles in the container-holder may be dictated by, among other things, considerations of intended throughput and desired time period between required re-stocking of supplies. Containers in fluid drawer 300 may be identified by machine-readable code, such as RFID. An indicator panel 307 having visible signals (e.g., red and green LEDs) and/or other indicators (textual, audible, etc.) be provided on frame 302 or in fluid drawer 300 (or on the container-holders) to provide feedback to the operator regarding container status. Indicator panel 307 may be positioned at any location in the fluid drawer 300 or the container-holders (note different exemplary locations of indicator panels 307 in FIGS. 1B and 2).

In some embodiments, diagnostic system 10 may include a container holder transporter 700 (see, e.g., FIGS. 2, 9, 12, and 13) that is configured to move one or more container-holders (e.g., container-holder 500 or container-holder 600) from frame 302 of fluid drawer 300 to another location in diagnostic system 10. As shown in FIGS. 2, 9, 12, and 13, for example, holder transporter 700 can be positioned adjacent container-holder 500 near the back end of frame 302 when frame 302 is at the closed position. Holder transporter 700 is described further below.

Figure 4A:
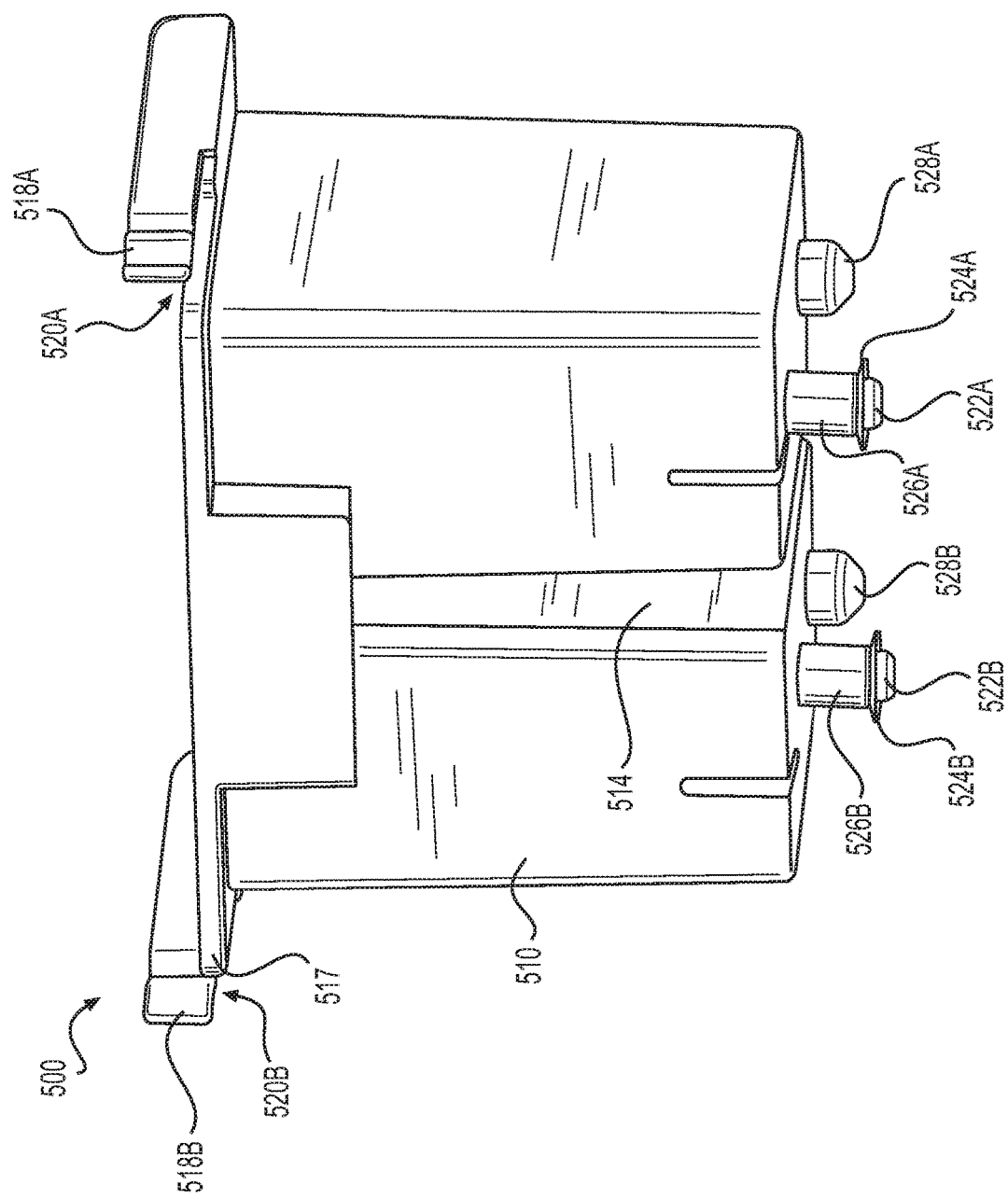
FIGS. 4A-4E are different views of an exemplary container-holder, according to an embodiment.
Figure 4B:
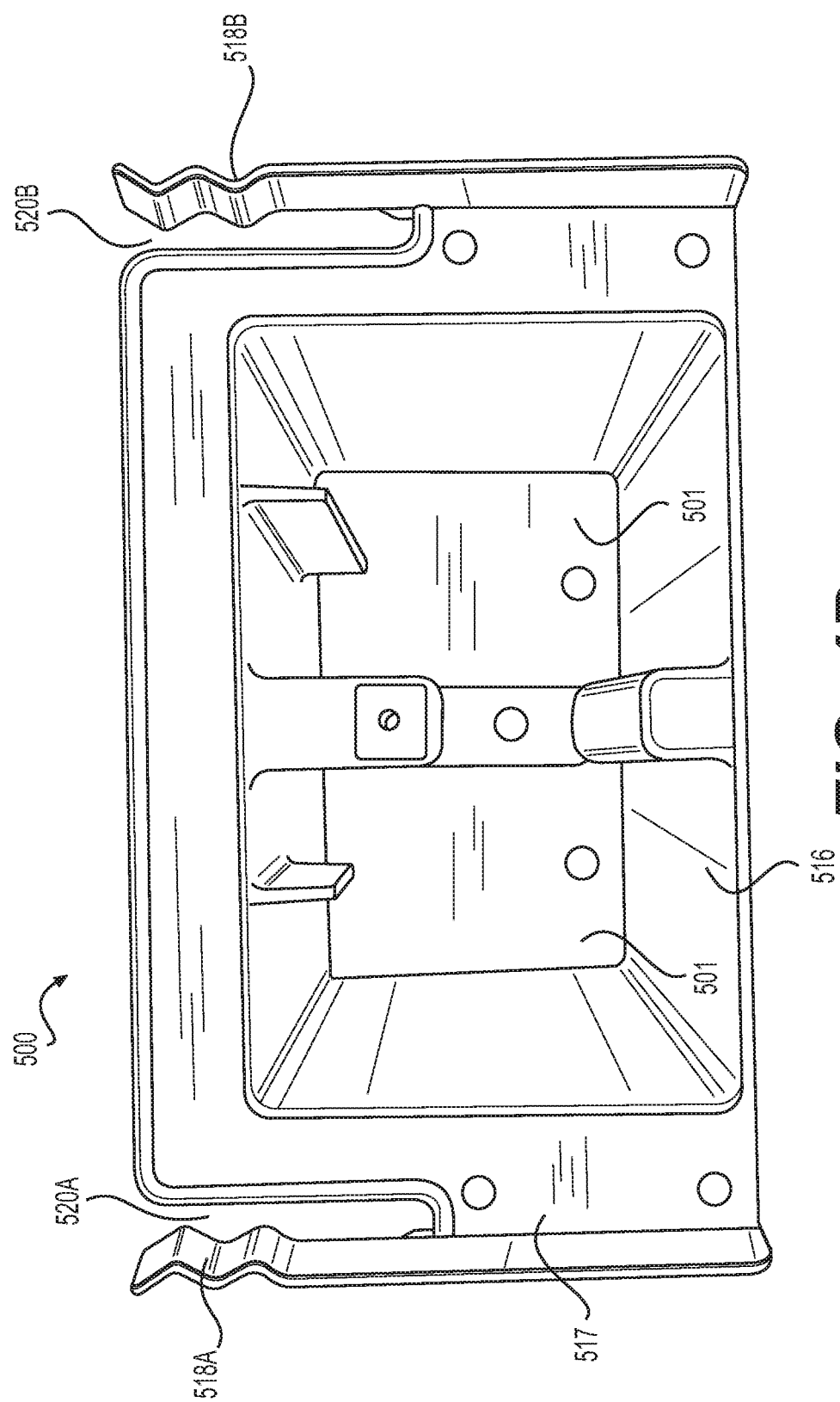
Figure 7:
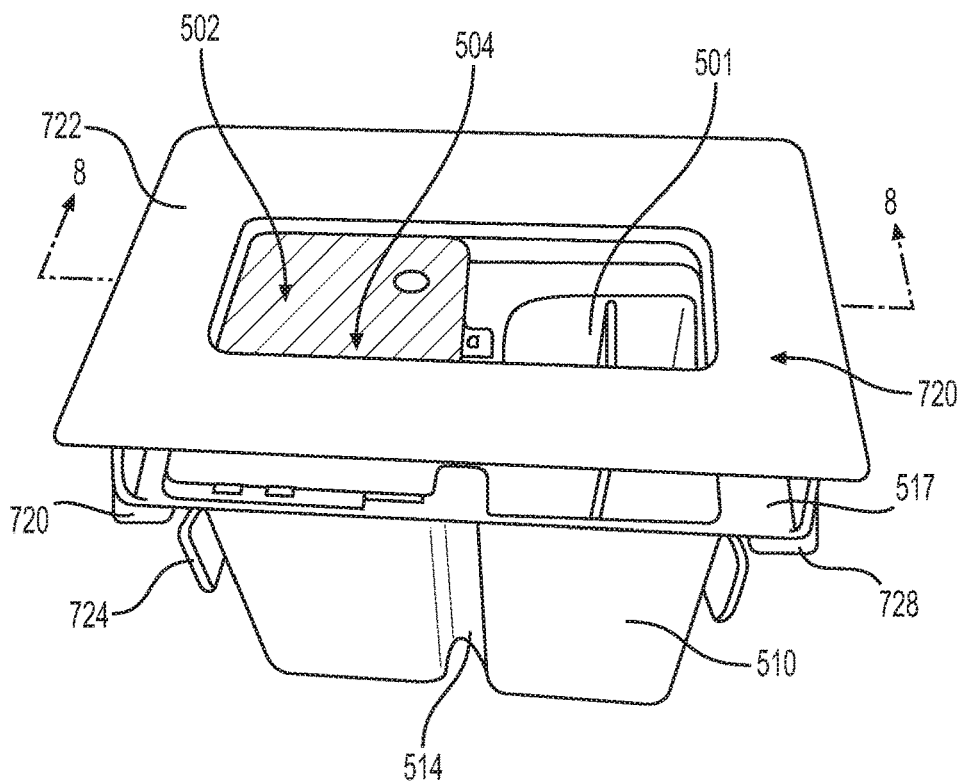
FIG. 7 is a front perspective view of a holder support coupled with a container holder, according to embodiment.

FIGS. 4A-4E and 7 illustrate different views of container-holder 500 according to various embodiments. FIG. 7 illustrates an exemplary container-holder 500 (for example, an elution buffer container-holder) with an exemplary container 502 (for example, a container filled with an elution buffer) in one of its receptacles 501, and FIGS. 4A-4E illustrate an exemplary container-holder 500 without any containers 502 in its receptacles 501. Referring collectively to FIGS. 4A-4E and 7, container-holder 500 may include a base or a tub portion 510 that forms the two receptacles 501 for receiving the fluid containers 502, and a flange 517 extending outwardly from a top portion of tub portion 510. As best seen in FIG. 4B, flange 517 may extend around the left and right lateral sides and back side of tub portion 510 in some embodiments. Container-holder 500 can define at least one channel. For example, container-holder 500 can define a pair of channels 520A and 520B on the left and right lateral sides of container-holder 500. In some embodiments, channels 520A and 520B are defined in flange 517 and are bounded, at least in part, by a pair of spring arms 518A and 518B, respectively. Channels 520A and 520B may extend in a direction that is substantially parallel with the direction frame 302 travels between the opened position and the closed position. Accordingly, channels 520A and 520B may receive pins 730 of transporter 700 (described further below) as frame 302 moves to the closed position.

Further, although container-holder 500 of FIGS. 4A-4E and 7 have receptacles 501 with generally rectangular cross-sectional shapes, this is only exemplary. In general, receptacles 501 may have any shape (e.g., a cross-sectional shape of rectangular, square, polygon, circular, oval, etc.) and size configured to receive a desired fluid container. In some embodiments, as illustrated in FIG. 7 (and FIGS. 4A-4E), opposing side surfaces and the bottom surface of container-holder 500 may include a crevice 514 (or a valley) that separates the two receptacles 501. However, crevice 514 is only exemplary. In some embodiments, crevice 514 may be omitted, and the side and/or bottom surface of container-holder 500 may include a continuous surface. Typically, the shape and size of receptacles 501 may match the shape and size of the desired fluid-filled containers 502 (for example, containers filled with elution buffer) that will be received in receptacles 501. In some embodiments, an RFID tag may be attached to a surface of the container-holder 500.

Figure 4C:
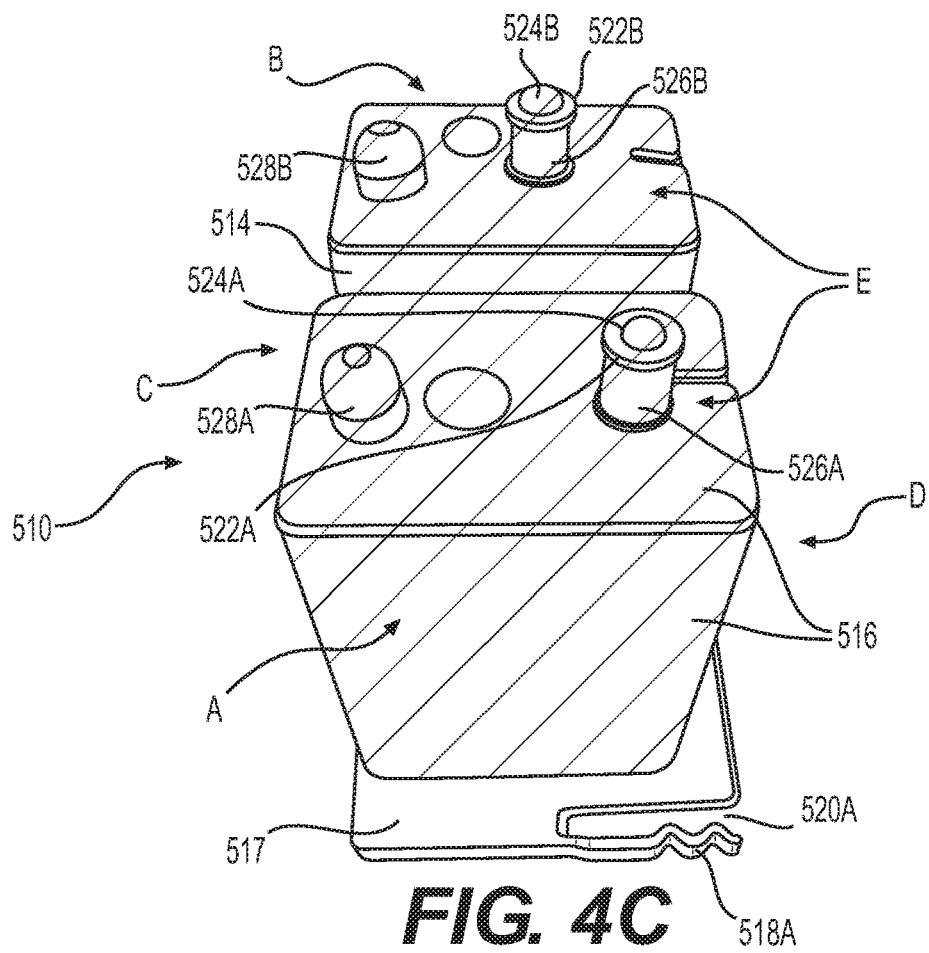
Figure 4D:
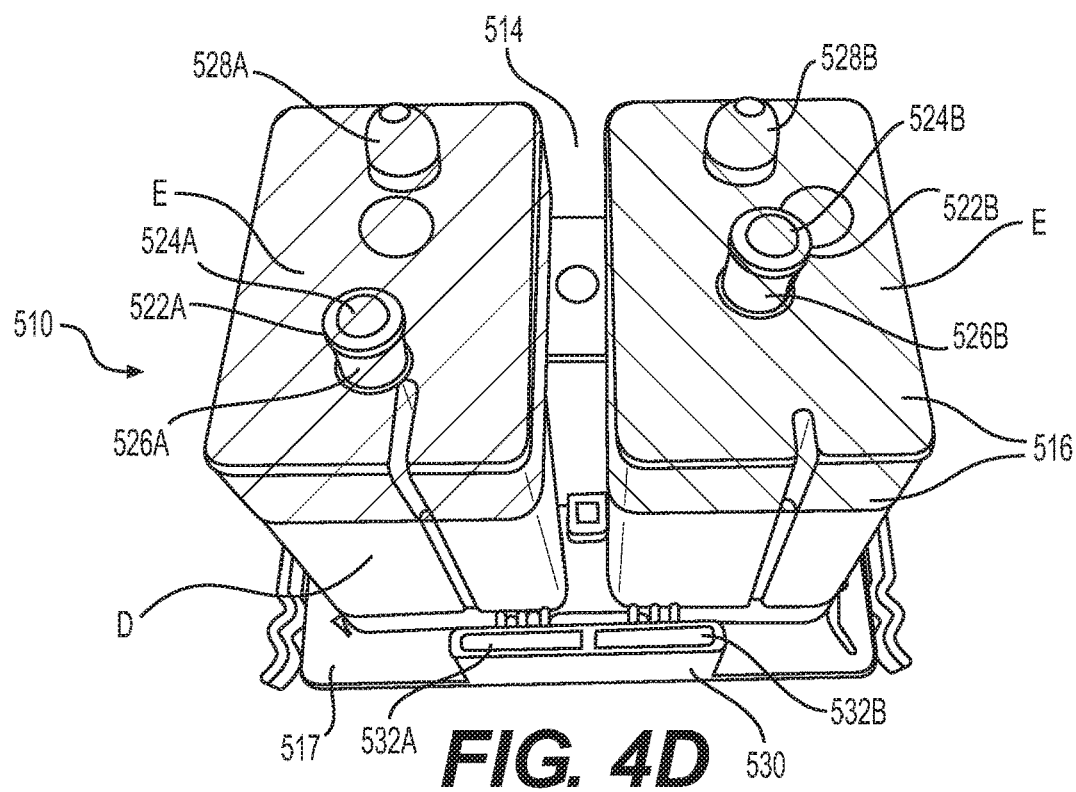

As best seen shown in FIGS. 4A, 4C, and 4D, container-holder 500 can include one or more knobs extending from bottom wall E of container-holder 500 in some embodiments. For example, container-holder 500 can include a pair of spaced apart knobs 522A and 522B extending from bottom wall E. Knob 522A can be aligned with one receptacle 501, and knob 522B can be aligned with the other receptacle 501. Each knob 522A and 522B has a respective post portion 526A and 526B extending from bottom wall E, and a flange 524A and 524B extending outwardly from the distal end of post portion 526A and 526B. As described further below, knobs 522A and 522B can be used to lock container-holder 500 to frame 302.

In some embodiments container-holder 500 includes a second pair of spaced apart knobs 528A and 528B extending from bottom wall E. Knob 528A can be aligned with one receptacle 501, and knob 528B can be aligned with the other receptacle 501. Although knobs 528A and 528B are illustrated with dome-like shapes, knobs 528A and 528B can have other shapes, for example, cylindrical or conical shapes. As described further below, knobs 528A and 528B can be used to register (i.e., align) the position of container-holder 500 relative to frame 302.

Figure 4E:
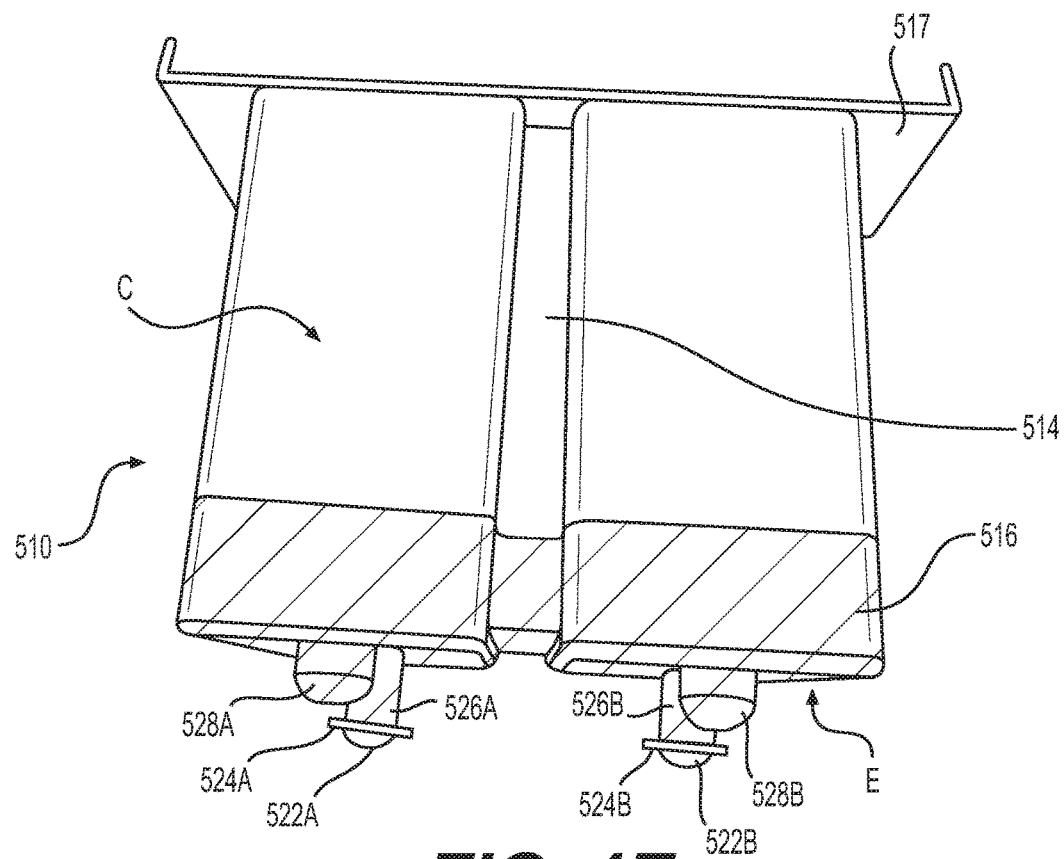

FIG. 4C is a bottom perspective view of container-holder 500, including tub portion 510, showing the side wall A and the bottom wall E. FIGS. 4D and 4E are another bottom perspective view and front perspective view of container-holder 500, including tub portion 510, showing the side walls D and C, respectively. Again, in some embodiments, tub portion 510 may be formed from an electrically non-conductive material (e.g., plastic). In some embodiments, tub portion 510 body has a at least one conductive outer surface for connection to an electrical ground or voltage source, and in some embodiments, container-holder 500 is not formed solely of an electrically conductive metal.

For example, as illustrated in FIGS. 4C-4E, one or more of side walls A, B, C, and D, and bottom wall E of container-holder 500 may include metallized portions 516. As illustrated in FIG. 4C, in some embodiments, substantially the entire outer surface of opposing side walls A and B and bottom wall E may include a metallized portion 516. And, as illustrated in FIGS. 4D and 4E, at least a portion of an outer surface of opposing side walls C and D may include a metallized portion 516. Metallized portion 516 in these figures is illustrated using hatched lines on a surface. Metallized portions 516 of surfaces of side walls C and D and metallized portions 516 of surfaces of side walls A and B may be adjacent to metallized portion 516 of the surface of bottom wall E. That is, the metallized portions 516 of the surfaces of bottom wall E and side walls A, B, C, and D may form a contiguous surface. In some embodiments, as illustrated in FIGS. 4C-4E, the surfaces of side walls C and D and the surface of bottom wall E within crevice 514 may also include a metallized portion 516. However, in some embodiments, some or all of the surfaces within crevice 514 may not include a metallized portion 516. For example, in some embodiments, surfaces of crevice 514 on side walls C and D may not include metallized portions 516, and surfaces of crevice 514 on bottom wall E may include a metallized portion 516.

Metallized portion 516 may be formed by covering a portion of wall of tub portion 510 (e.g., side wall A, B, C, D, or bottom wall E) with a layer of an electrically conductive metal. The metal layer of a metallized portion 516 may have any suitable thickness. In some embodiments, the thickness of a metallized portion 516 may be between about 0.5-2.0 mils thick. However, this thickness is only exemplary. In different embodiments of the current disclosure, metallized portion 516 may have any value of thickness between about 0.2-10 mils. Metallized portion 516 may be affixed to a surface by any method. In some embodiments, a metal foil (e.g., an aluminum foil, copper foil, steel foil, etc.) may be attached to a wall of tub portion 510 using an adhesive layer. For example, in some embodiments, an aluminum foil (or a foil of another electrically conductive material) with an adhesive face may be attached to a surface of a wall (side walls, bottom wall, etc.) of tub portion 510 to form a metallized portion 516. In some embodiments, a surface of a tub wall (side wall, bottom wall, etc.) may be coated with a metal layer (aluminum, steel, copper, etc.) using any known coating process (e.g., electroless plating, vapor deposition, painted using conductive paint, etc.) to form a metallized portion 516.

Any region of side walls A, B, C, and D may include a metallized portion 516. Although FIG. 4C illustrates substantially an entire surface (i.e., substantially 100% of the area) of side wall A and bottom wall E as having a metallized portion 516, this is only exemplary. Similarly, although FIGS. 4D and 4E illustrate that about 20-30% of the length of side walls C and D includes a metallized portion 516, this is only exemplary. In general any suitable amount of the outer surface of side walls A, B, C, and D may include metallized portions 516. For example, in some embodiments, about 5-20%, 20-30%, 40-50%, 50-75%, 75-100% of the surface (e.g., length, area, etc.) of side walls A, B, C, and D may include metallized portions 516. In some embodiments, only selected surfaces of tub portion 510 (e.g., bottom wall E) may include a metallized portion 516. Further, although FIGS. 4C-4E illustrate the metallized portion 516 as being formed on an external surface of tub portion 510, this is only exemplary. In some embodiments, alternate to or in addition to these metallized portions 516, the walls (portions of the walls or substantially all of the walls) of tub portion 510 may be formed of an electrically conductive metal or fabricated using a conductive plastic. For example, in some embodiments, conductive metal inserts may be included in a plastic molding to form bottom wall E and/or portions of side walls A, B, C, and D.

Figure 5A:
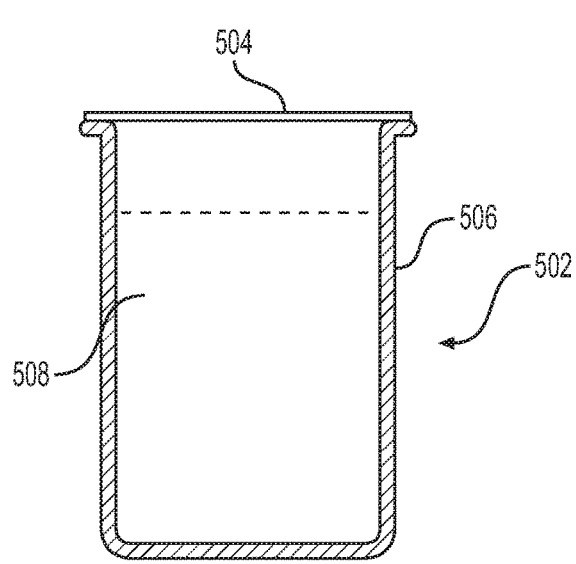
FIGS. 5A and 5B are schematic cross-sectional views of exemplary reagent filled containers used in the system of FIG. 1A, according to an embodiment.
Figure 5B:
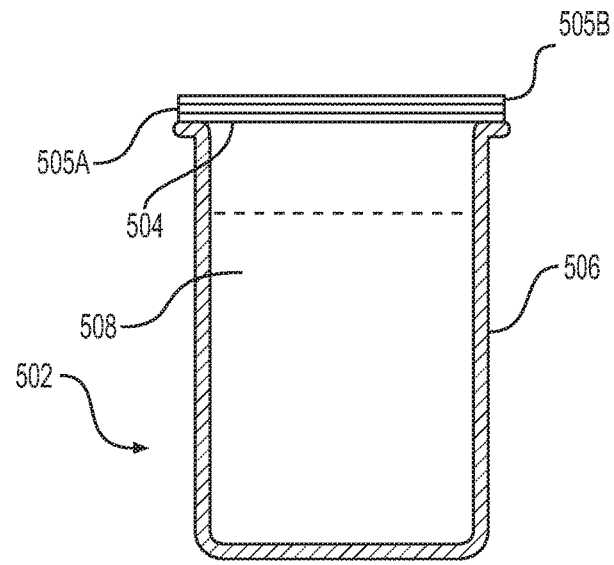

FIGS. 5A and 5B illustrate cross-sectional schematic views of exemplary fluid containers 502 (for example, containers filled with elution buffer) that may be placed in receptacles 501 of container-holder 500. Fluid containers 502 may include a cup-like reservoir 506 that contains fluid 508 (for example, elution buffer), and a sealing foil 504 that covers the mouth of the reservoir. In some embodiments, container 502 may be structurally similar to a yogurt cup with a foil lid that encloses the fluid within the cup. During use, a probe tip (for example, an integrally formed pipette tip or releasably coupled disposable pipette tip) of a fluid transfer device (for example, a robotic pipettor (similar to pipettor 200 shown in FIG. 1A)) penetrates through sealing foil 504, to form hole in the sealing foil (visible in the sealing foil 504 of FIG. 7), to access fluid 508 in container 502. In some embodiments in which the probe tip is a releasably coupled disposable pipette tip, the tip is formed of conductive plastic. In some embodiments, as illustrated in FIG. 5B, sealing foil 504 of container 502 may be covered by an elastomeric sheet 505A, forming, for example, an elastomeric septum. In some embodiments, the elastomeric sheet 505A may include a slit (i.e., may be precut) for the probe tip to pass through. In such embodiments, the probe tip may pass through the slit in sheet 505A and penetrate foil 504 under the slit to enter container 502. In some embodiments, the probe tip may tear and create a slit (or a flap) on elastomeric sheet 505A as it enters container 502. The slit on the elastomeric sheet, which overlies the hole on sealing foil 504 (formed by the probe tip), may reduce evaporation of fluid 508 from container 502. In some embodiments, elastomeric sheet 505A may be covered by a rigid plastic cover 505B with a septum or an opening to provide access to the probe tip of the pipettor (see FIG. 3). In such embodiments, to access fluid 508 in container 502, the tip of the pipettor may pass through elastomeric sheet 505A and foil 504 through the hole or septum of rigid plastic cover 505B. Fluid container 602, which may contain a reconstitution solution, may be similar in structure to containers 502 of FIGS. 5A and 5B, which may contain an elution buffer in some embodiments. That is, reconstitution fluid container 602 may have cup-like reservoir with a cover in the form of a sealing foil 604 (similar to sealing foil 504 of FIG. 5A), or a sealing foil covered by an elastomeric sheet 605A and a plastic cover 605B (similar to FIG. 5B).

Figure 6:
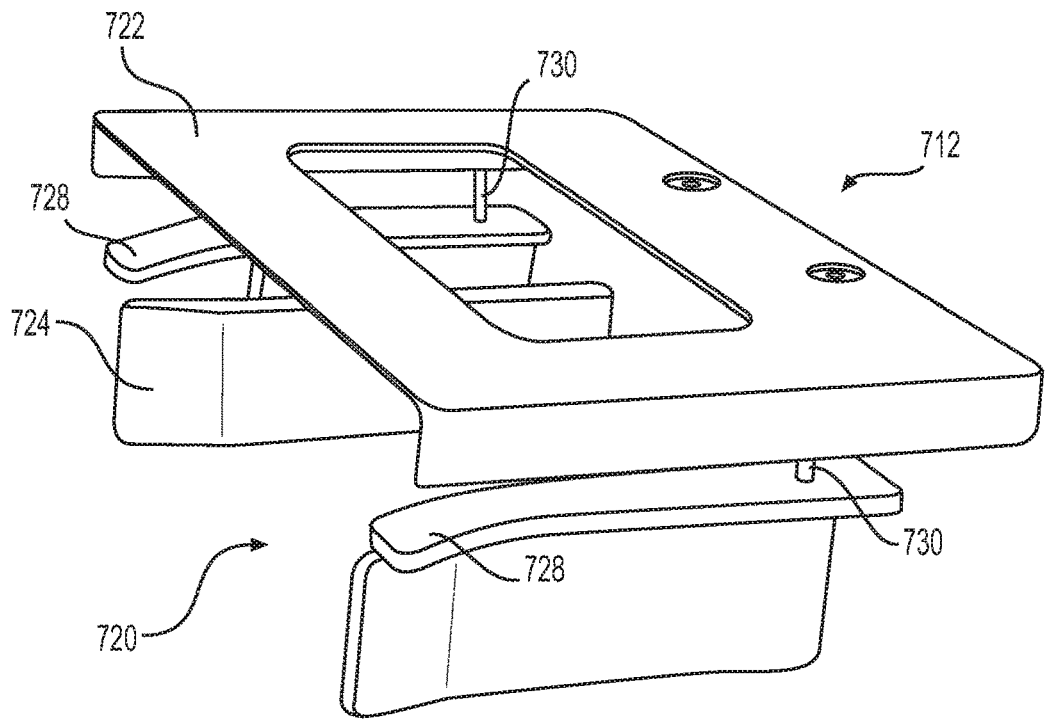
FIG. 6 is a side perspective view of a holder support of a holder transporter, according to an embodiment.
Figure 8:
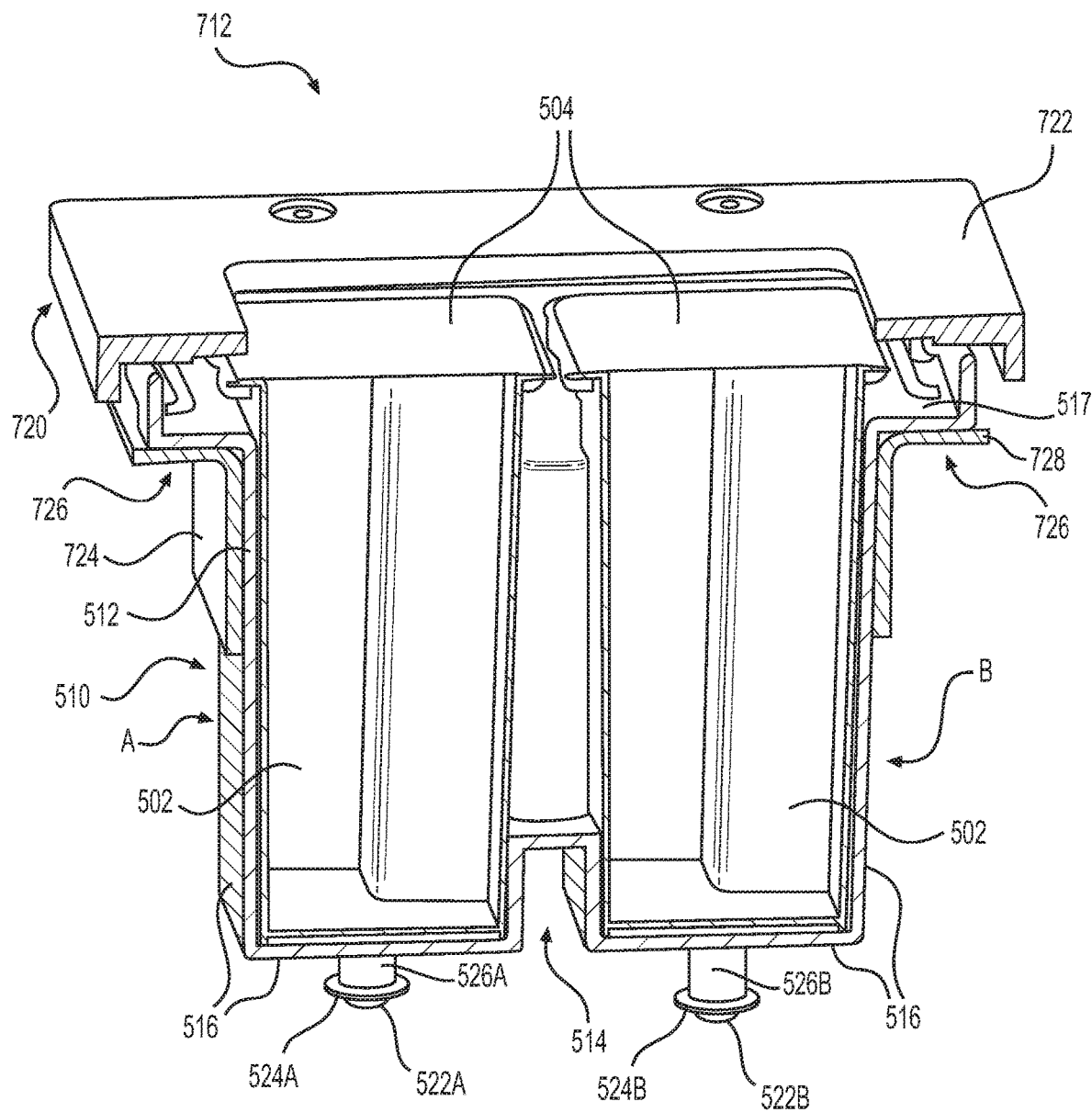
FIG. 8 is a front cross-sectional view of the holder support coupled with the container holder taken along line 8-8 in FIG. 7.

In some embodiments, transporter 700 includes a holder support 720 configured to releasably and securely coupled with container-holder 500 when frame 302 is at the closed position. An exemplary holder support 720 is illustrated in FIGS. 6, 7, and 8. Holder support 720 may be fixed when frame 302 of fluid drawer 300 is pulled out to the opened position so that tub portion 510 of container-holder 500 slides out from holder support 720, and allows the operator to load containers 502 into receptacles 501. Holder support 720 may be oriented (relative to tub portion 510) such that a portion of holder support 720 inhibits withdrawal (for example, in the upward vertical direction) of containers 502 from within receptacles 501. As illustrated in FIG. 6, holder support 720 may include a top portion 722 and a bottom portion 724 spaced apart from top portion 722. Top portion 722 and bottom portion 724 can be spaced apart by a pair of pins 730 (shown in FIG. 6). In other embodiments, top portion 722 may be attached to bottom portion 724 (or to system 10) using mechanical fasteners (screws, etc.) or any other suitable method. It is also contemplated that, in some embodiments, top portion 722 and bottom portion 724 may be formed as a single integral part.

The volume of space defined between top portion 722 and bottom portion 725 is configured to receive a portion of container-holder 500, for example, the top portion of container-holder 500 including flange 517, as frame 302 moves to the closed position. In some embodiments, bottom portion 724 of holder support 720 forms ledges 726 on opposite sides of container-holder 500. Ledges 726 can include surfaces 728 that support container-holder 500 when holder support 720 is coupled to container-holder 500. As the top portion of container-holder 500, including flange 517, is received in the volume of space defined between top portion 722 and bottom portion 724, pins 730 slide within respective channels 520A and 520B defined by flange 517, and flange 517 rests against surfaces 728 of bottom portion 724. In some embodiments, spring arms 518A and 518B are configured to create an interference fit (e.g., a snap fit) with respective pins 730 received within channels 520A and 520B. As best seen in FIG. 4B, the distal ends of spring arms 518A and 518B can include protrusions to assist in creating the interference fit with pins 730. This interference fit releasably secures container-holder 500 to holder support 720 of transporter 700, inhibiting movement of container-holder 500 in a direction towards the opened position until a threshold force is exceeded. Accordingly, container-holder 500 can move along with holder support 720 without becoming disengaged therefrom.

In some embodiments, top portion 722 may be made of an electrically nonconductive material (e.g., plastic), and bottom portion 724 may be made of an electrically nonconductive material or an electrically conductive material (e.g., aluminum, iron, steel, copper, etc.).

Top portion 722 may have any shape and configuration, and when fixed relative to tub portion 510, may inhibit removal of container 502 from receptacle 501, for example, in an upward vertical direction. In some embodiments, as illustrated in FIGS. 6 and 7, top portion 722 may have a window-frame shape with an opening (for example, a rectangular opening) that exposes a portion of container 502 therethrough (see FIG. 7). However, the window frame shape is only exemplary. In general, top portion 722 may have any shape and configuration such that, when holder support 720 is fixed relative to tub portion 510, at least a portion of top portion 722 overlies a portion of container 502 in receptacle 501 and exposes at least a portion of the fluid containing receptacles of container 502.

With reference to FIG. 7, after a container 502 (e.g., the containers shown in FIG. 5A or 5B) is placed in a receptacle 501 of tub portion 510, holder support 720 can be attached to the top of container 502 such that a portion of top portion 722 of holder support 720 overlies the outer perimeter portion of container 502. Top portion 722 forms a window-frame shaped opening exposing a region of sealing foil 504 and/or a portion of elastomeric sheet 505A (if the container of FIG. 5B is used). The portion of top portion 722 that overlies container 502 inhibits (or prevents) withdrawal of container 502 from receptacle 501 (e.g., in the upward vertical direction when a fluid transfer device is withdrawn in an upward direction from container 502 after extracting fluid from container 502). In some embodiments, the portion of top portion 722 that overlies container 502 presses down on the underlying area of sealing foil 504 (or rigid plastic cover 505B if the container of FIG. 5B is used). In embodiments in which top portion 722 is made of an electrically nonconductive material and bottom portion 724 is made of an electrically conductive material, top portion 722 serves to electrically insulate (or separate) sealing foil 504 from bottom portion 724 of holder support 720. In embodiments in which top portion 722 and bottom portion 724 of holder support 720 are both electrically conductive (e.g., holder support 720 is a single component made of a conductive material such as metal), an insulating layer (e.g., insulating tape, washer, etc.) may be positioned between the mating surfaces of top portion 722 and sealing foil 504 to insulate sealing foil 504 from holder support 720. Although holder support 720 is described as being attached to transporter 700, holder support 720 may be attached to any component of system 10 and oriented (with respect to tub portion 510) such that a portion of holder support 720 overlies a container 502 positioned in a receptacle 501 of tub portion 510.

FIG. 8 illustrates an exemplary cross-sectional schematic view of a container-holder 500 with containers 502 in its receptacles. When holder support 720 is coupled to container-holder 500, bottom portion 724 of holder support 720 contacts a contact region 512 on the metallized portions 516 of side walls A and B of tub portion 510 (see also FIG. 16). The contact region 512 may extend over any length or area of the surface of tub side walls A, B. In some embodiments, the contact region may extend from between about 10-30% of the length (or area) of the surface of side walls A, B. However, it is also contemplated that, in some embodiments, contact region 512 may extend over a greater length or area (e.g., about 40-60%, etc.) of the surface of side walls A, B. In some embodiments, holder support 720 may be configured such that bottom portion 724 contacts side walls C and D in addition to side walls A and B. In some such embodiments, the metallized portions on side walls C and D may extend over substantially the entire surface of side walls C and D (similar to side walls A and B).

When holder support 720 is attached to container-holder 500, metal bottom portion 724 of holder support 720 can be electrically connected to an outer conductive surface of container-holder 500, for example, bottom wall E of tub portion 510 through the metallized portions 516 on side walls A and B. This contact enables the formation of an electrically conductive plane or circuit around tub portion 510 of container-holder 500. This conductive plane is electrically insulated from sealing foils 504 (of containers 502 in receptacles 501) by the nonconductive top portion 722 of holder support 720. In embodiments in which the metallized portion 516 is primarily on the bottom wall E, the electrically conductive plane may be formed primarily by bottom wall E. In some embodiments, ledge 726 may be positioned on the same side as contact regions 512 (i.e., on opposite side walls A and B, or on the same sides where bottom portion 724 of holder support 720 contacts the side wall). However, in some embodiments, ledge 726 may be formed on more than the two opposite sides (e.g., all four sides, etc.) of container-holder 500.

When frame 302 of fluid drawer 300 is at the closed position (as shown in FIG. 1A and FIG. 2), holder support 720 of holder transporter 700 (see FIG. 2) engages container-holder 500 to move container-holder 500 between a position on frame 302 (for example, when seated in recess 632) in fluid drawer 300 in second module 400 to a position 150 in first module 100. FIG. 9 illustrates an exemplary holder transporter 700 engaged with container-holder 500 in fluid drawer 300 when frame 302 is at the closed position. Holder transporter 700 includes one or more arms 704 that operatively couple an actuator 702 to holder support 720. At least one of arms 704 is coupled to actuator 702 such that actuator moves arms 704. In some embodiments, actuator 702 is an electric motor that rotates at least one of arms 704. For example, referencing FIG. 9, transporter 700 includes two arms 704. One end of the right arm in FIG. 9 is fixedly coupled to the drive shaft of an electric motor 702, and one end of the left arm is pivotably coupled to a portion of system 10. The other ends of the right and left arms 704 are pivotably coupled to holder support 702. Accordingly, as electric motor 702 rotates the right arm 704, the arm 704 moves holder support 720. Due to the connection points of arms 704, holder support 720 travels along an arcuate path that includes both a vertical component and a horizontal component. That is, referencing FIG. 9, the holder support 720 (and thus container-holder 500 and containers 502 coupled thereto) moves in either the upward and downward vertical directions (i.e., the vertical component) concurrently with moving in either the left or right horizontal directions (i.e., the horizontal component). In other embodiments, arms 704 can be configured such that holder support 720 moves along other non-arcuate paths that include a vertical component.

Figure 10:
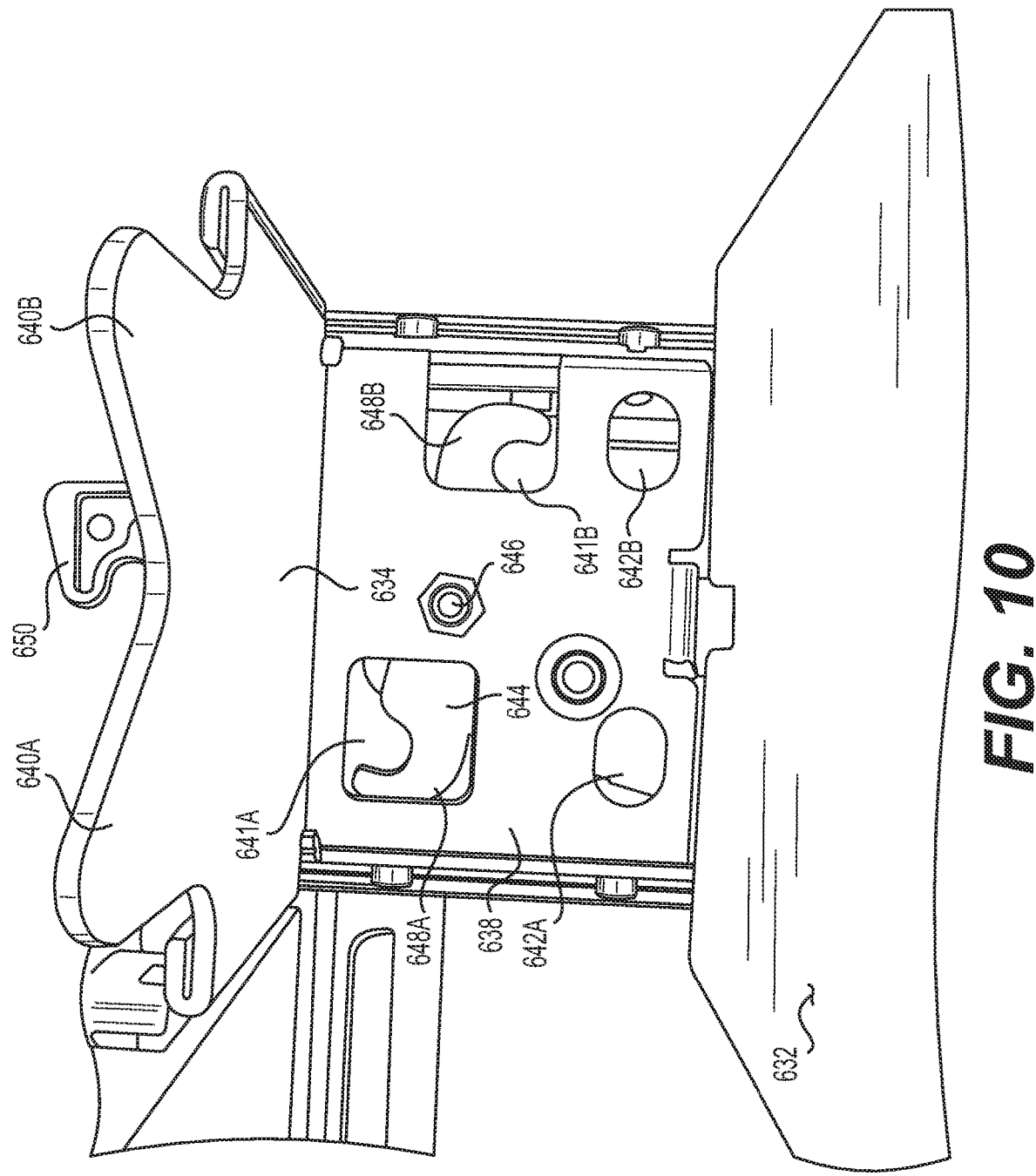
FIG. 10 is a top perspective view of a back end of a frame of a fluid drawer with a locking arm at an unlocked position, according to an embodiment.
Figure 11:
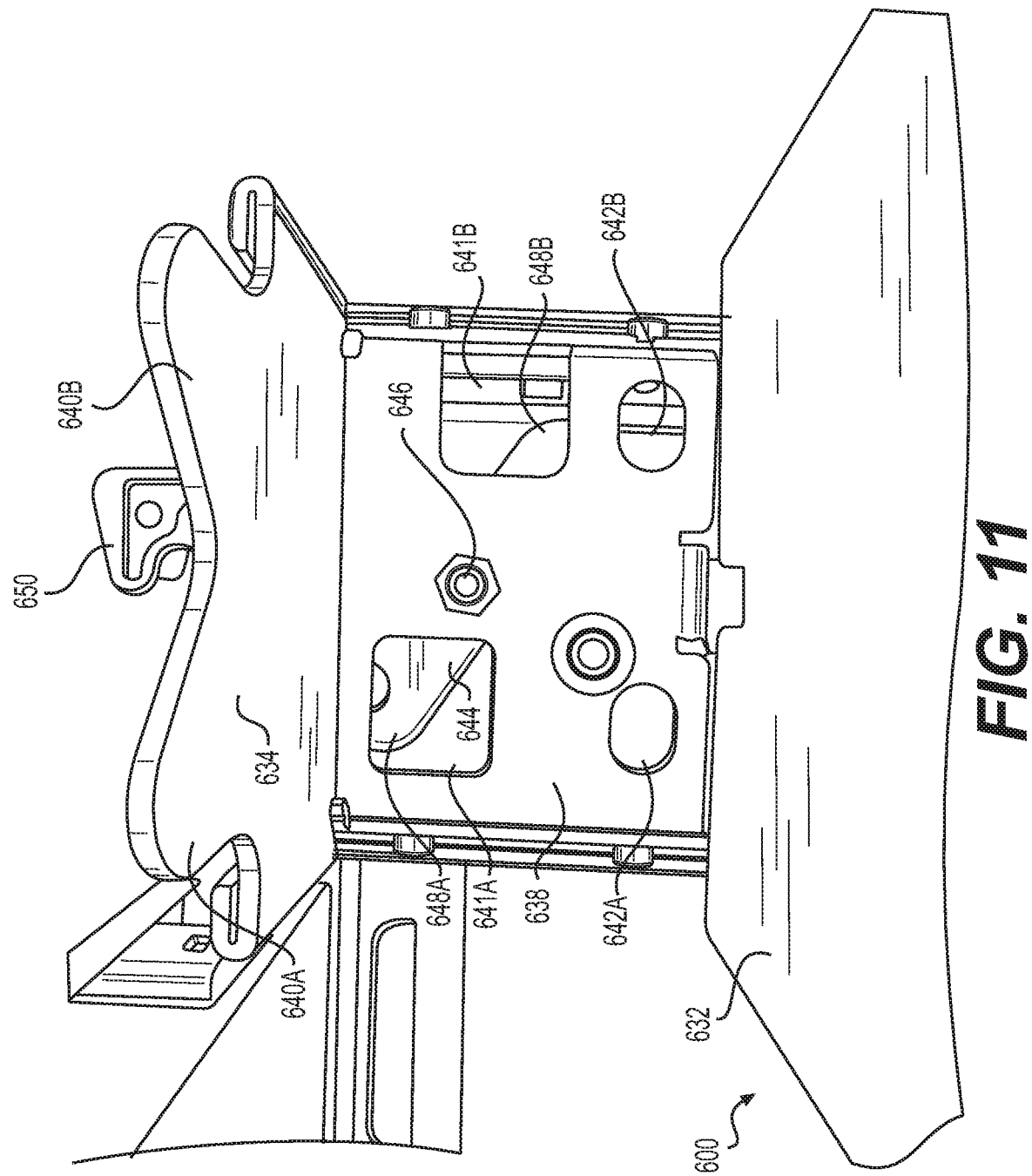
FIG. 11 is a top perspective view of the back end of the frame of the fluid drawer in FIG. 10 with the locking arm at a locked position, according to an embodiment.

In some embodiments, frame 302 includes a holder interface component that engages container-holder 500 to align and/or support container-holder 500 relative to frame 302. For example, as shown in FIGS. 9, 10, and 11, panel 634 of frame 302 can include a pair of protrusions 640A and 640B. And as shown in FIG. 4D, container-holder 500 can include a portion 530 extending downward from flange 517 in use (but upward in the orientation of FIG. 4D), and portion 530 defines a pair of slots 532A and 532B. Slots 532A and 532B and protrusions 640A and 640B are configured such that when container-holder 500 is seated within recess 636, slots 532A and 532B receive at least the upper portions of protrusions 640A and 640B, respectively. Because holder support 720 moves along a path that includes a vertical component, holder support 720 can be lifted up thereby removing the upper portions of protrusions 640A and 640B, from slots 532A and 532B, respectively.

In some embodiments, arms 704 are pivotably coupled to structural members of second module 400 that are electrically coupled to components (e.g., the housing of second module 400) connected to the system ground (i.e., arms 704 are electrically grounded). Upon activation of holder transporter 700, arms 704 engage with holder support 720 via bearings 710 and move container-holder 500 from a position on frame 302 at the closed position within fluid drawer 300 to a position 150 within first module 100. When arms 704 are thus engaged with holder support 720, the electrically conductive plane of container-holder 500 formed by its metallized portions 516 (for example, on side walls A and B, and/or bottom wall E) are electrically connected to the system ground (or is grounded) through metal bottom portion 724 of holder support 720, bearings 710, and arms 704. In the discussion below, this grounded electrically conductive plane formed on tub portion 510 is referred to as the ground plane.

Figure 15:
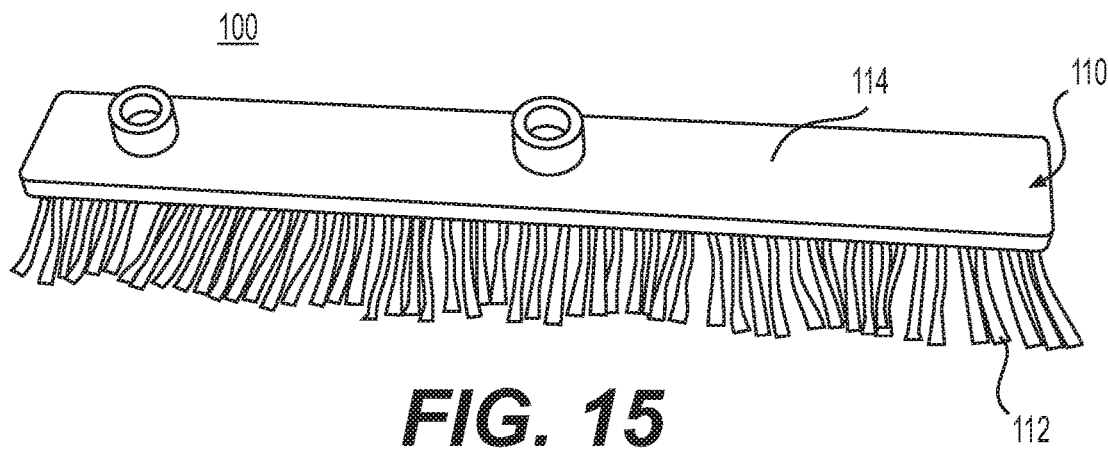
FIG. 15 is a perspective view of an exemplary conductive brush, according to an embodiment.

In some embodiments, as illustrated in FIG. 9, when container-holder 500 is positioned at location 150, an electrically conductive brush 110 of diagnostic system 10 may make electrical contact with a metallized portion 516 on the side walls (e.g., side wall B) of tub portion 510. Brush 110 may be attached to a component of system 10 that is connected to the system ground, and thus may be electrically grounded. In some embodiments, brush 110 may be attached to a component of first module 100. FIG. 15 illustrates an exemplary brush 110. Brush 110 may include bristles 112 attached to a base 114. The base 114 may be attached to a grounded component of first module 100, via any suitable mechanism permitting an electrically conductive path, such that bristles 112 make contact with a metallized portion 516 on a side wall (e.g. side wall B) of tub portion 510 when elution buffer container-holder 500 is positioned at location 150 in first module 100. In embodiments where a brush 110 is used, electrical contact between the grounded brush 110 and the metallized portion 516 of side wall B may provide an additional (or an alternate) grounding path for the ground plane.

Figure 16:
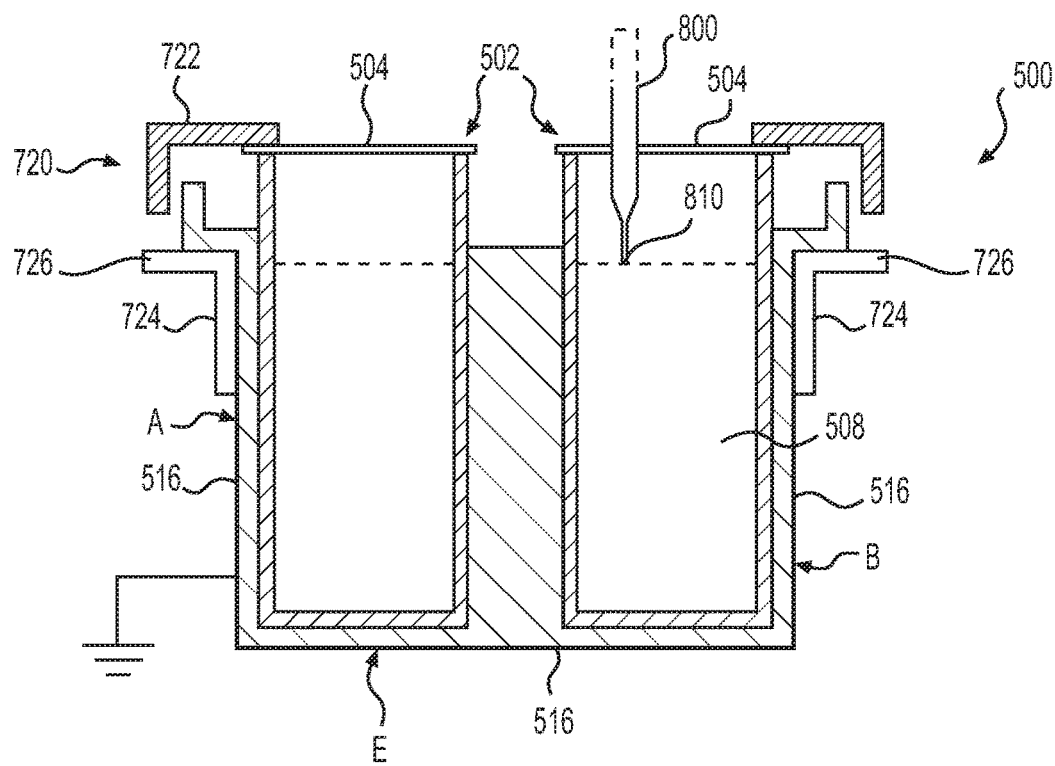
FIG. 16 is a schematic cross-sectional view of container, a holder, a holder support of a transporter, and a robotic pipettor performing capacitive fluid level sensing in the container, according to an embodiment.

When container-holder 500 is positioned at position 150 in first module 100, a fluid transfer device (for example, an automated robotic pipettor 800) of first module 100 may be used to extract a desired quantity of fluid 508 (for example, elution buffer or any other desired reagent) from container 502. Since the structure and operation of a pipettor is described in the publications incorporated by reference herein, it is not described herein. FIG. 16 is a schematic illustration of a robotic pipettor 800 extracting fluid 508 from fluid container 502 in container-holder 500. Pipettor 800 includes a probe tip 810 that is configured to penetrate through at least sealing foil 504 of container 502 to access fluid 508 in container 502. After withdrawing a desired quantity of fluid 508, under control of a control system of system 10, pipettor 800, including probe tip 810, is withdrawn from container 502, and is transported to a different location of system 10, to transfer the withdrawn fluid to, for example, a receptacle or vial for analysis of samples. As is known to people in the art, during operation of system 10, pipettor 800 may access and withdraw fluid 808 from container 502 numerous times, thereby decreasing the quantity of fluid 508 in container 502. During withdrawal of pipettor 800 from container 502, the portion of holder support 720 that overlies container 502 may inhibit vertical movement of container 502 relative to receptacle 501 and container-holder 500.

In some embodiments, fluid drawer 300 also includes a holder lock that secures container-holder 500 to frame 302 when frame 302 is at the opened position (see FIG. 1B) and that unlocks container-holder 500 from frame 302 when frame 302 is at the closed position (see FIG. 1A). A lock having this configuration allows transporter 700 to move container-holder 500 between a position within recess 636 on frame 302 (when frame 302 is at the closed position) to position 150 in first module 100, while also securing container-holder 500 to frame 302 as an operator to remove containers 502 from receptacles 501 of container-holder 500 without decoupling holder 500 from frame 302.

Figure 12:
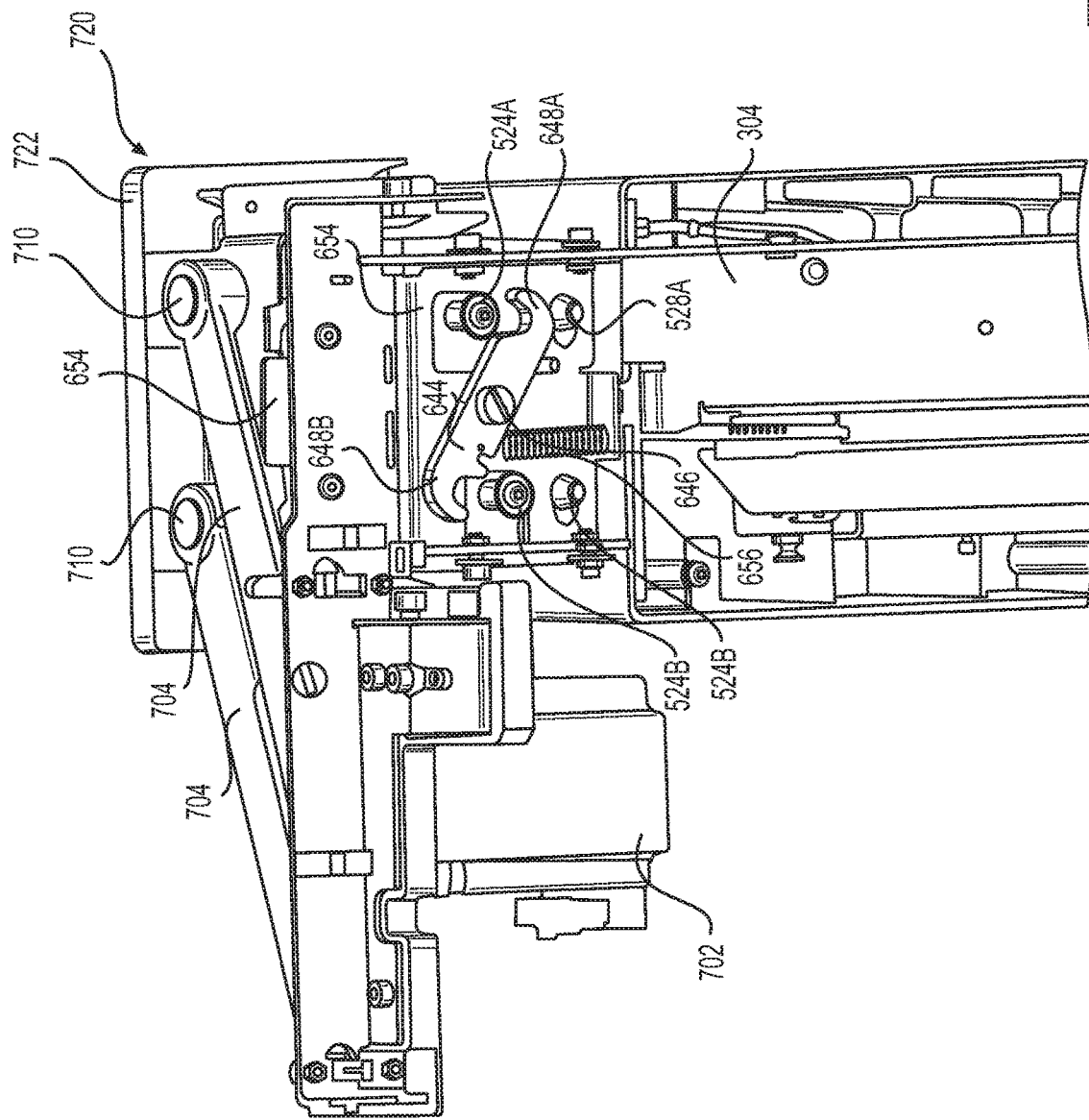
FIG. 12 is a bottom perspective view of the back end of the fluid drawer with a locking arm at an unlocked position, according to an embodiment.
Figure 13:
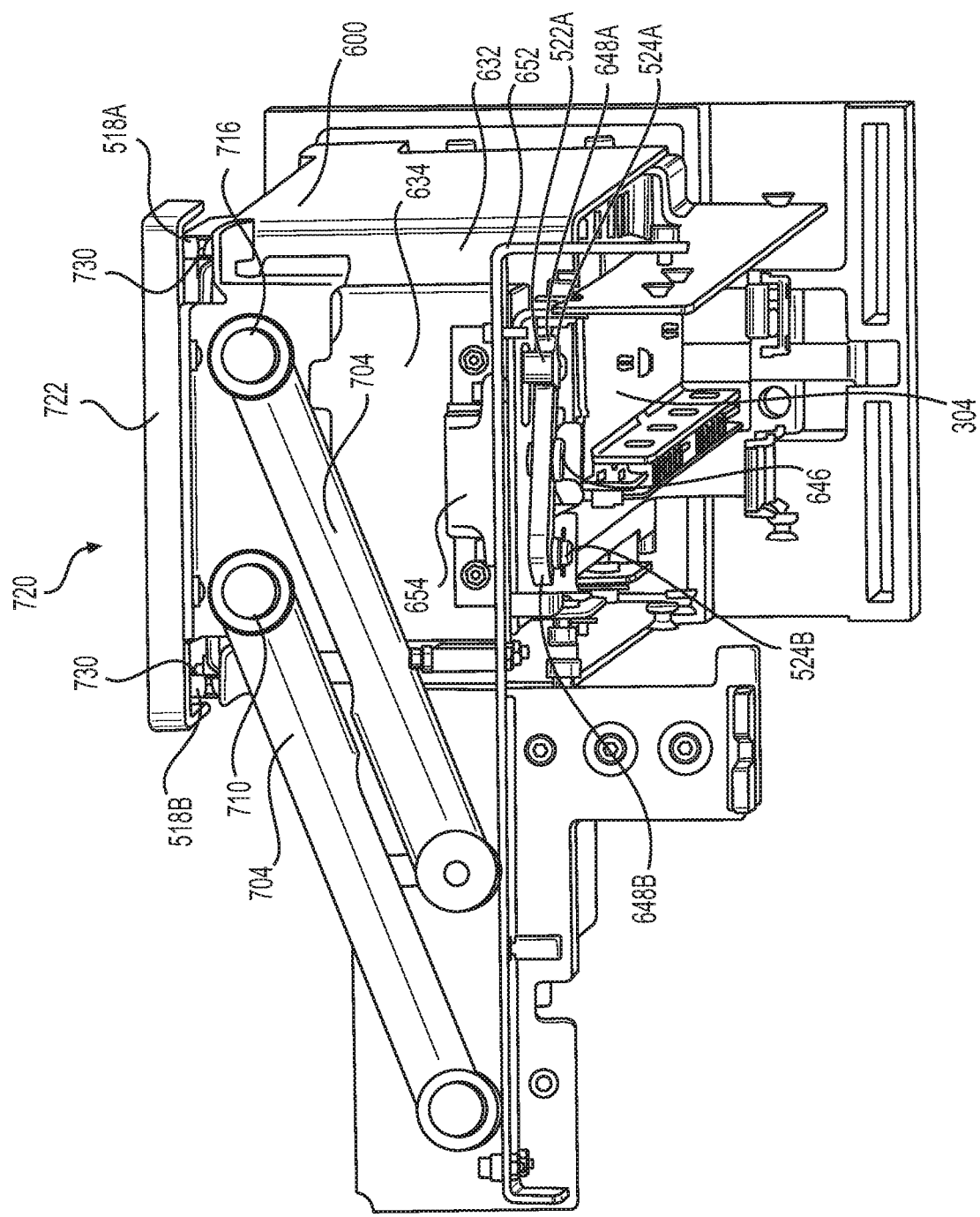
FIG. 13 is a rear perspective view of the back end of the fluid drawer with a locking arm at a locked position, according to an embodiment.

In some embodiments, base panel 638, which defines in part recess 636 that receives container-holder 500, defines a plurality of openings 641A, 641B, 642A, and 642B configured to receive there through knobs 522A, 522B, 528A, and 528B of container-holder 500 when container-holder 500 is received in recess 636. As shown in FIGS. 12 and 13, knobs 522A, 522B, 528A, and 528B extend from a top side of base panel 638 to a bottom side of base panel 638 when container-holder 500 is received in recess 636. In such embodiments, flanges 524A and 524B of knobs 522A and 522B are spaced a distance away from the bottom surface of panel 638. In such embodiments, the holder lock can include at least one arm 644 movably coupled to frame 302. For example, arm 644 can be pivotably coupled to a bottom side of frame 302 using a pivot pin 646 the defines the axis about which arm 644 rotates. Arm 644 is movable relative to openings 641A and 641B between two arm positions—locked and unlocked arm positions.

In some embodiments, at a locked arm position (see, for example, FIGS. 11 and 13), arm 644 engages a portion of knob 522A extending through opening 641A, thereby securing container holder 500 to the frame. In some embodiments, arm 644 also engages a portion of knob 522B extending through opening 641B, at the first arm position. For example, in some embodiments, arm 644 includes a first hook 648A at one end of arm 644 and a second hook 648B at the other end of arm 644. At the locked arm position, first hook 648A can engage a portion of knob 522A extending through opening 641A between flange 524A and the bottom surface of base panel 638, and second hook 648B can engage portion of knob 522B extending through opening 641B between flange 524B and the bottom surface of base panel 638. As such, first and second hooks 648A and 648B overlap (in the vertical direction) flanges 524A and 524B, thereby inhibiting upward vertical movement of knobs 522A and 522B of container-holder 500 relative to frame 302, and locking container-holder 500 to frame 302.

In some embodiments, at an unlocked arm position (see, for example, FIG. 12), arm 644 is disengaged from knobs 522A and 522B extending through opening 641A and 641B, thereby unlocking container-holder 500 from frame 302. In some embodiments, at the unlocked arm position, arm 644 is reoriented such that first hook 648A disengages the portion of knob 522A extending through opening 641A between flange 524A and the bottom surface of base panel 638, and second hook 648B disengages the portion of knob 522B extending through opening 641B between flange 524B and the bottom surface of base panel 638. And at the unlocked arm position, neither first hook 648A nor second hook 648B overlaps (in the vertical direction) a portion of flanges 524A and 524B, thereby allowing upward vertical movement of knobs 522A and 522B of container-holder 500 relative to frame 302, and unlocking container-holder 500 from frame 302.

In some embodiments, arm 644 is biased to the locked arm position. For example, in some embodiments, a spring 656 is coupled between arm 644 and a portion of frame 302 in a manner that biases arm 644 to the locked arm position as shown in FIG. 12. In other embodiments (not shown), arm 644 is biased to the unlocked arm position.

Figure 14:
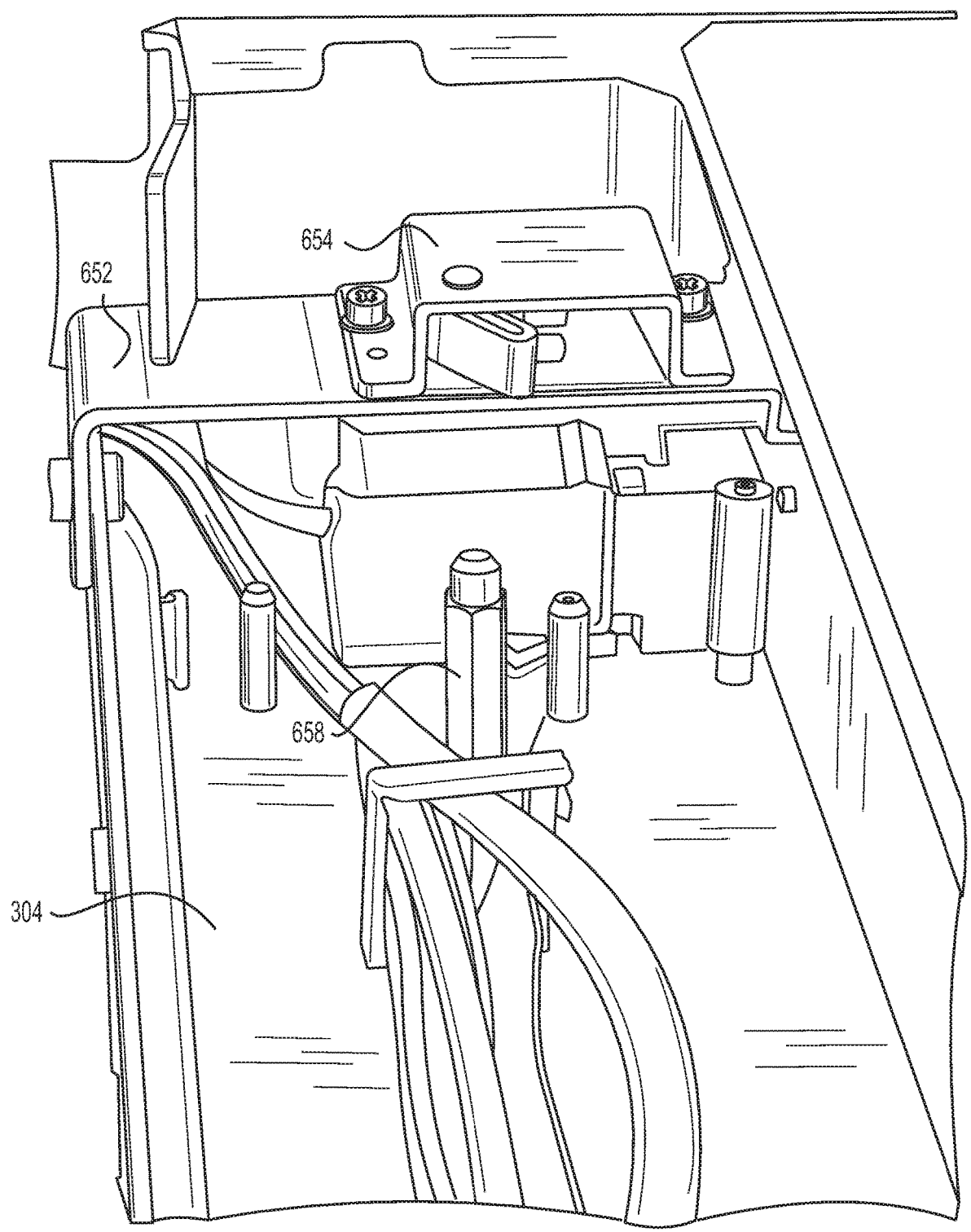
FIG. 14 is a front perspective view of a back end of a frame of a fluid drawer, according to an embodiment.

In some embodiments, the holder lock is passively (without using an active actuator) actuated between the locked and unlocked arm positions. For example, as shown in FIG. 14, stationary support 304 of fluid drawer 300 can include a fixed pin 658 extending upward from the base of stationary support 304. Pin 658 is positioned such that, as frame 302 approaches the closed position (see FIG. 1A), pin 658 engages arm 644. For example, pin 658 can be positioned near the back end of frame 302 when frame 302 is at the closed position. As frame 302 continues to the closed position, pin 658 contacts arm 644, thereby pivoting arm 644 about the pivot pin 646, thereby moving the arm 644 to the unlocked arm position. And as frame 302 is moved from the closed position to the opened position, pin 658 disengages arm 644 allowing arm 644 to pivot and return to the locked arm position.

In some embodiments (not shown), the holder lock is actively actuated (using an active actuator) between the locked and unlocked arm positions. For example, in some embodiments, an actuator can be coupled to frame 302 and arm 644. Either as frame 302 approaches the closed position (see FIG. 1A) or after frame 302 reaches the closed position, a control signal can be transmitted to the actuator that then moves arm 644 to the unlocked arm position, for example, by applying a force with a movable element. And when movement of frame 302 from the closed position back to the opened position is started, a control signal can be transmitted to the actuator that then moves arm 644 back to the locked arm position.

In some embodiments, fluid drawer 300 also includes a frame lock to inhibit movement of frame 302 relative to stationary support 304 when container-holder 500 is unlocked from frame 302. In some embodiments, the frame lock includes one locking component fixed to the stationary support 304, and a complementary locking component fixed to frame 302. For example, the frame lock may include a hook 650 fixedly coupled to a back end of frame 302, and a catch 654 fixedly coupled to a portion 652 of station support 304. Catch 654 is configured to receive hook 650 in a manner such that movement of frame 302 relative to stationary support 304 is inhibited. Although in the illustrated embodiments, hook 650 is coupled to frame 302 and catch 654 is coupled to stationary support 304, catch 654 can be coupled to frame 302, and hook 650 can be coupled to stationary support 304. Pipettor 800 may be adapted to detect the level of fluid 508 in container 502 using capacitive level sensing (and, in some cases, other fluid level sensing or measurement techniques). Since the theory and operation of capacitive level liquid sensing is known in the art, it is not described in detail herein. Probe tip 810 of pipettor 800, which is connected to an alternating current, serves as one plate of a capacitor, and the ground plane (e.g., the grounded electrically conductive plane formed on tub portion 510 by its metallized portions 516), serves as the other plate of the capacitor. The capacitance signal (a signal related to the capacitance) measured between these two plates may be used to measure the fluid level in container 502. In embodiments in which fluid 508 is conductive (for example, a conductive elution buffer), when probe tip 810 makes contact with the surface of fluid 508, a spike is observed in the capacitance signal. As the capacitance is inversely proportional to the distance between the plates, as the fluid level in container 502 decreases, the spike in the observed capacitance signal (or the strength of the signal) increases. In use, as probe tip 810 of the pipettor moves downward seeking fluid, the position (height) of the pipettor 800 (e.g., pipettor arm) is monitored simultaneously along with the capacitance signal. When the capacitance signal increases rapidly (e.g., a spike likely caused by probe tip 810 contacting fluid), the height of the pipettor is noted, thus establishing the height of the fluid surface. Since one plate of the capacitor, or the ground plane, is positioned very close to the base of container 502 (e.g., bottom wall E), the measured capacitance signal is very sensitive to, and therefore may be used to detect the fluid level in container 502 accurately. Thus, providing metallized portions 516 on the boundary walls, or the base, of container-holder 500 improves the accuracy and sensitivity of fluid level measurement in container 502.

Electrical contact of probe tip 810 with sealing foil 504 (of container 502) also results in a capacitance signal (entry-related capacitance signal). Probe tip 810 contacts sealing foil 504 when it first penetrates sealing foil 504 to form an opening in it. Due to accumulated droplets of fluid 508 around the opening (e.g., transferred from probe tip 810 to the opening as the wet probe tip 810 repeatedly passes through the opening), an entry-related capacitance signal may also be observed every time probe tip 810 passes through the opening. This entry-related capacitance signal is unrelated to the fluid level in container 502, and should therefore be distinguished from the fluid level-related capacitance signal (resulting from probe tip 810 contacting fluid 508 in container 502) for accurate fluid level measurement. Electrically isolating (insulating or separating) sealing foil 504 from the ground plane using the nonconductive top portion 722 of holder support 720 reduces the magnitude of (and in some cases substantially eliminates) the entry-related capacitance signal, thereby improving the accuracy of the fluid level measurement (see FIGS. 8 and 17).

Figure 17:
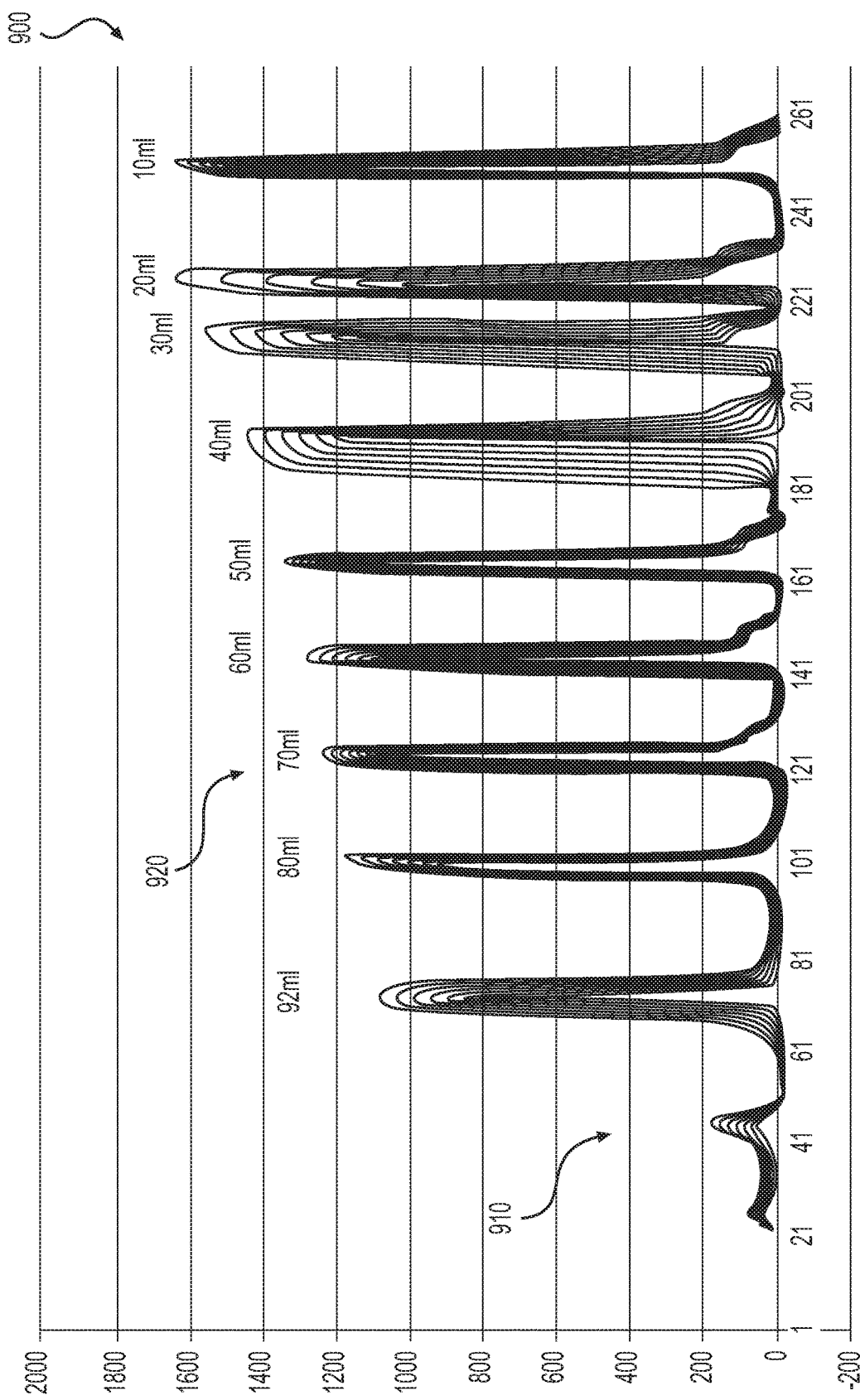
FIG. 17 is a schematic illustration of the exemplary capacitance signals observed during capacitive fluid level sensing, according to an embodiment.

FIG. 17 is a graph 900 illustrating the capacitance signals observed between probe tip 810 and the ground plane during multiple trials using an exemplary embodiment. Each curve in graph 900 includes the signals observed during a single trial. The y-axis of the graph 900 is the magnitude of the observed capacitance signal in arbitrary units, and the x-axis is an indicator of the spatial location of probe tip 810 in arbitrary units from an arbitrary datum. As can be seen in FIG. 17, both entry-related capacitance signals 910 and fluid level-related capacitance signals 920 can be observed in graph 900. However, since the entry-related capacitance signals 910 are of substantially smaller magnitude than fluid level-related capacitance signals 920, they can be easily distinguished. It can also be seen that the magnitude of fluid level-related capacitance signals 920 increase towards the right of graph 900. This increase is a result of the decreasing distance between probe tip 810 and the ground plane towards the right of the graph 900. Liquid height determination is related to pipettor position once a change in capacitance is measured. Using the observed capacitance signal and probe tip location, the fluid level in container 502 is determined. Since the peaks of the curves at each fluid level are spaced close together in the vertical direction, and the peaks at different fluid levels are vertically spaced apart from each other, the observed capacitance signals are very sensitive to the fluid level.

Experiments similar to those represented by graph 900 were conducted using container-holders 500 with different embodiments of metallized portions 516. These results indicate that providing metallized portions 516 on the boundary walls of tub portion 510, and electrically isolating sealing foil 504 from the ground plane, will result in capacitance signals that are a good (repeatable, reliable, etc.) indicator of fluid level in container 502. Although container-holders 500 used in these experiments had metallized portions 516 on at least a portion of the side walls of tub portion 510 (e.g., side walls A, B, C, and/or D, see FIGS. 4C-4E), providing a grounded metallized portion 516 on any wall of tub portion 510 proximate or adjacent to receptacle 501 (e.g., one or more side walls and bottom wall), and connecting this metallized portion 516 to the system ground will result in capacitance signals that can be used to accurately detect fluid level. For instance, in some embodiments, only the bottom wall E of tub portion 510 may be grounded (e.g., by providing a metallized portion 516 on only bottom wall E and connecting this metallized portion 516 to the system ground, for example, by brush 110). In some embodiments, only one of side walls A, D, C, or D may include a metallized portion 516 that is electrically connected to the system ground. In all these embodiments, the capacitance signals that result from probe tip 810 touching the fluid surface (along with the probe tip location) can be accurately used to determine the fluid level in the container.

It should be noted that although a metallized portion 516 is described as being grounded by connecting the metallized portion 516 to the system ground, this is not a requirement. Grounding of a metallized portion may be achieved by any means known in the art. For example, a metallized portion 516 may be achieved by connecting the metallized portion 516 to a voltage source isolated (not connected) from the electrical circuit of the capacitive fluid sensor (i.e., and not directly connected to the ground).

The description above describes the use of metallized portions 516 to enable accurate capacitive fluid level sensing of elution buffer fluid 508 in a container 502 positioned in a receptacle 501 of container-holder 500. With reference to FIG. 3, similar metallized portions may also be used to detect the fluid level in a reconstitution fluid container 602 (or an oil container) positioned in a receptacle 601 of reagent container-holder 600. As explained above, reconstitution fluid container 602 may be structurally similar to buffer fluid container 502 (described above with reference to, for example, FIGS. 5A and 5B).

Figure 18A:
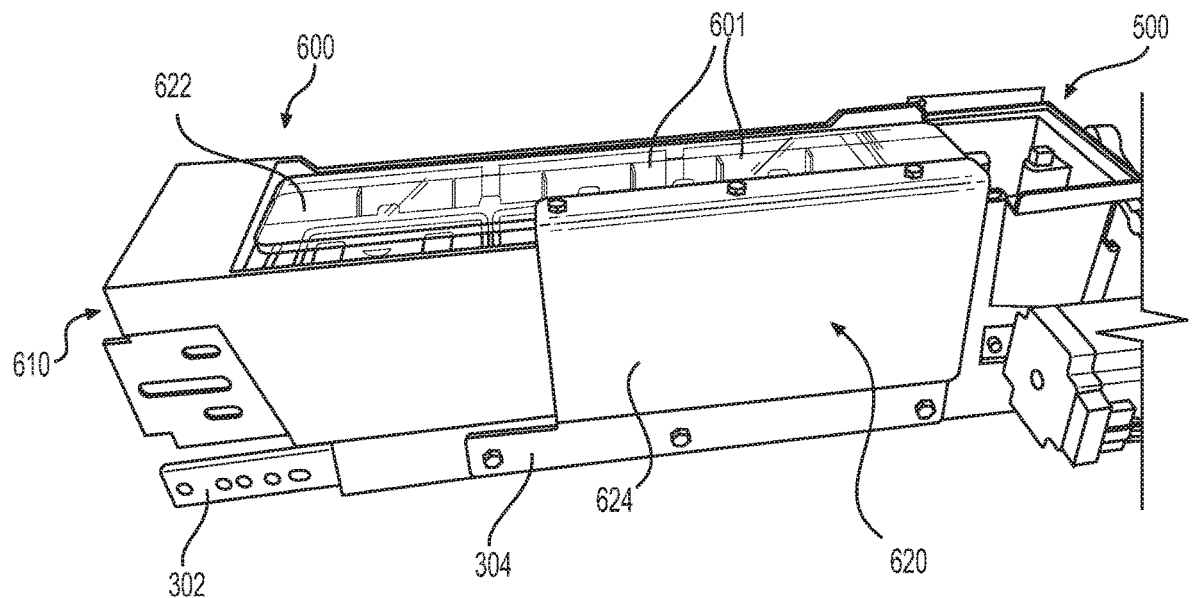
FIG. 18A is a perspective side view of an exemplary fluid drawer and reagent container-holders, according to an embodiment.
Figure 18B:
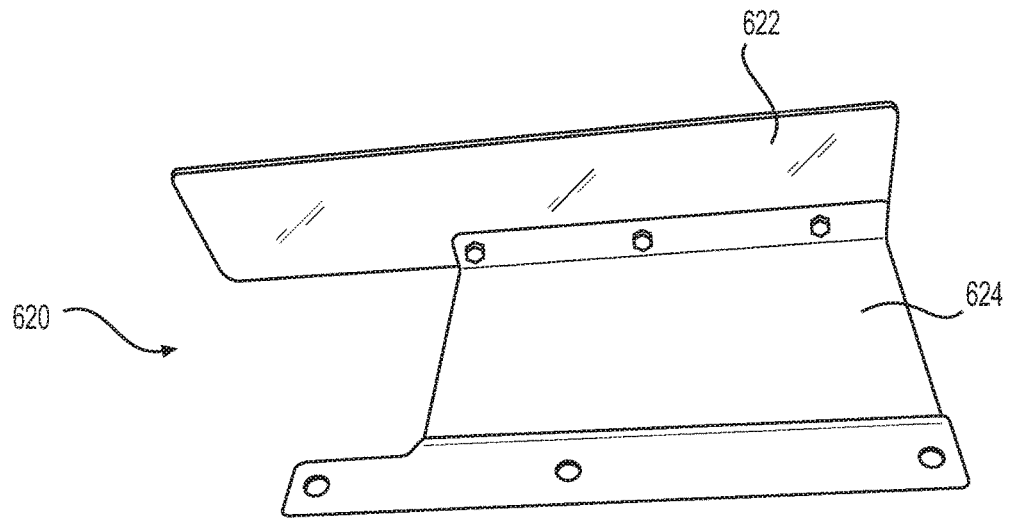
FIG. 18B is an exemplary lid of a reagent container-holder, according to an embodiment.

FIG. 18A illustrates a perspective view of reagent container-holder 600 with receptacles 601 for reconstitution fluid containers 602 and oil containers. Container-holder 600 may include a base or a tub portion 610 that includes receptacles 601, and a lid 620. Lid 620 is illustrated in FIG. 18B. Although not visible in FIG. 18A (visible in FIG. 19A), in some embodiments, opposing side surfaces of tub portion 610 may include crevices 614 that separate the receptacles. Typically, the shape and size of receptacles 601 may match the shape and size of the fluid filled containers that will be received in these receptacles. Lid 620 may be attached to a fixed module frame/chassis of module 400. When tub portion 610 is mounted or placed in the fluid drawer 300, the tub portion 610 may be slid out from under the lid 620, so that the operator can load and unload fluid packs (reconstitution fluid containers 602 and oil containers). In some embodiments, a similar lid/tub arrangement may also exist for the container-holder 500. In such embodiments, by sliding the fluid drawer 300 out, the tub portions 510 and 610 of both the elution buffer and reconstitution container-holders 500, 600 may be pulled out from under their lid 620 and holder support 720, thus enabling an operator to reload the containers therein. In some embodiments, the lid 620 may be attached to tub portion 610 or to another component of system 10 in any manner. In some embodiments, as illustrated in FIG. 18A, mechanical fasteners (e.g., screws, etc.) may be used to attach the lid to the chassis. In general, lid 620 may be attached to any component of system 10, and oriented relative to tub portion 610 such that a portion of lid 620 overlies a portion of a container 602 in a receptacle 601 of tub portion 610.

As illustrated in FIG. 18B, lid 620 may include an electrically nonconductive top portion 622 and a bracket portion 624. Bracket portion 624 may be formed of an electrically conductive or nonconductive material. In some embodiments, top portion 622 and bracket portion 624 may be two parts that are attached together to form lid 620. However, in some embodiments, lid 620 may be a single part with an integrated top portion 622 and bracket portion 624. Lid 620 may be attached to tub portion 620 at bracket portion 624. When bracket portion 624 is attached to tub portion 610, top portion 622 of lid 620 may extend over at least a part of the top surface of tub portion 610. As illustrated in FIG. 18B, in some embodiments, top portion 622 of lid 620 may extend substantially transverse to bracket portion 624. As can be seen in FIG. 3, when lid 620 is attached to tub portion 610 having a reconstitution fluid container 602 placed in a receptacle 601, a portion of the nonconductive top portion 622 overlies a portion of container 602 exposing a region of sealing foil 604. Although not a requirement, in some embodiments, the overlying region of top portion 622 may press down on the underlying region of container 602 to constrain the container in its receptacle. The probe tip of a robotic pipettor may penetrate through and extract the reconstitution fluid through the portion of sealing foil 604 exposed by top portion 622. As the probe tip withdraws, the portion of top portion 622 that overlies container 602 may prevent removal of container 602 from receptacle 601.

Figure 19A:
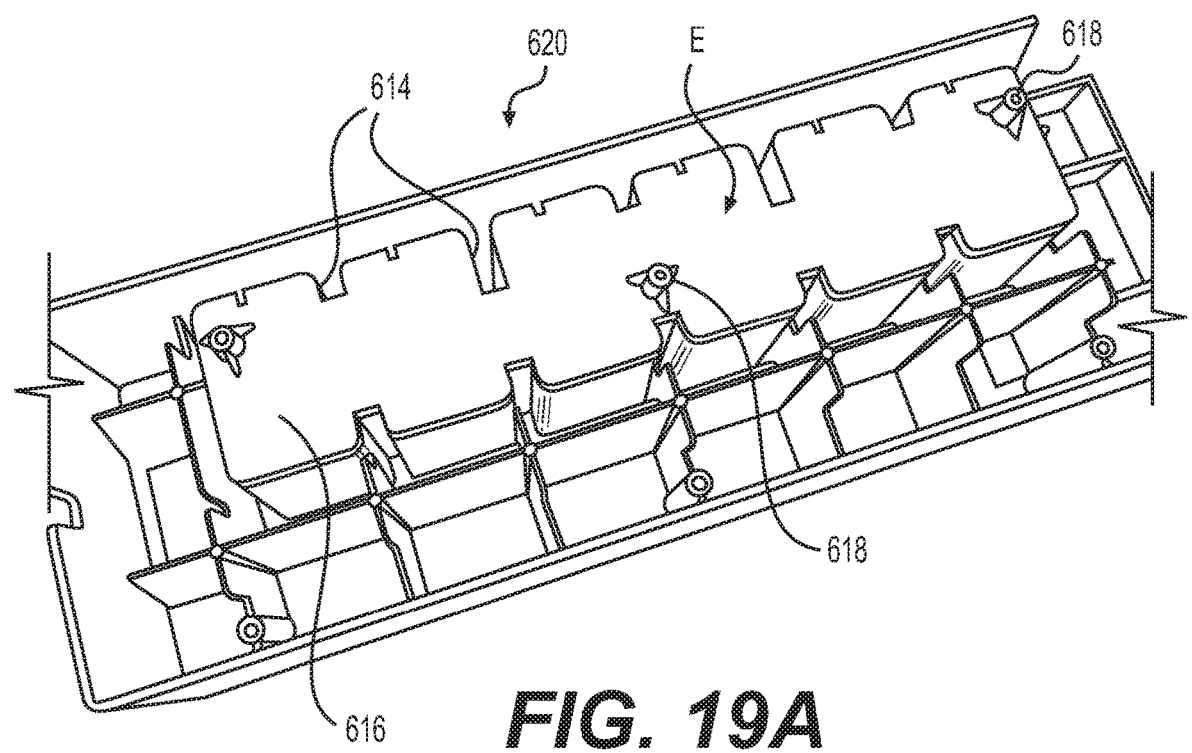
FIGS. 19A and 19B are illustrations of the bottom surfaces of exemplary reagent container-holder, according to an embodiment.

FIG. 19A illustrates tub portion 610 of reagent container-holder 600 showing its bottom wall E. The bottom wall E includes multiple knobs 618 that serve as alignment features for container-holder 600 in fluid drawer 300. Similar to that described with reference to container-holder 500, a metallized portion 616 may be provided on bottom wall E of container-holder 600. The metallized portion 616 may be substantially similar to the metallized portions 516 of container-holder 500, and may be formed in a similar manner. That is, metallized portion 616 may comprise a conductive metal foil (e.g., aluminum foil) attached to the bottom wall E using an adhesive, or may be layer of a conductive metal (copper, aluminum, etc.) coated or painted on surface E. It is also contemplated that, in some embodiments, the metallized portion 616 may be a part of the wall of container-holder 600. For example, some or all portions of wall E may be made of an electrically conductive material or include conductive material inserts.

Figure 19B:
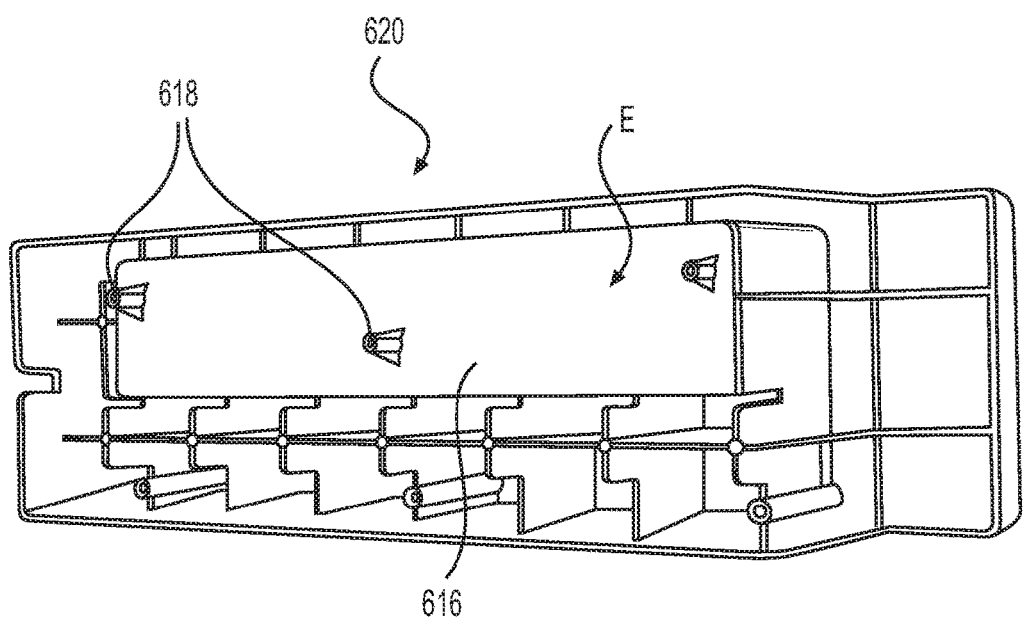

In some embodiments, as illustrated in FIG. 19A, the metallized portion 616 may have a shape substantially similar to bottom wall E (i.e., metallized portion 616 will not be formed over crevices 614). FIG. 19B illustrates another embodiment of container-holder 600 with a metallized portion 616 on its bottom wall E. As illustrated in FIG. 19B, in some embodiments, metallized portion 616 on bottom wall E may extend over, and cover, crevices 614. In some embodiments, metallized portion 616 may only be formed on bottom wall E of tub portion 610. However, in some embodiments, the metallized portion 616 may extend to one or more of the external side walls of receptacles 601 (similar to metallized portions 516 on side walls C and D of the container-holder 500 illustrated in FIGS. 4D and 4E).

Figure 20:
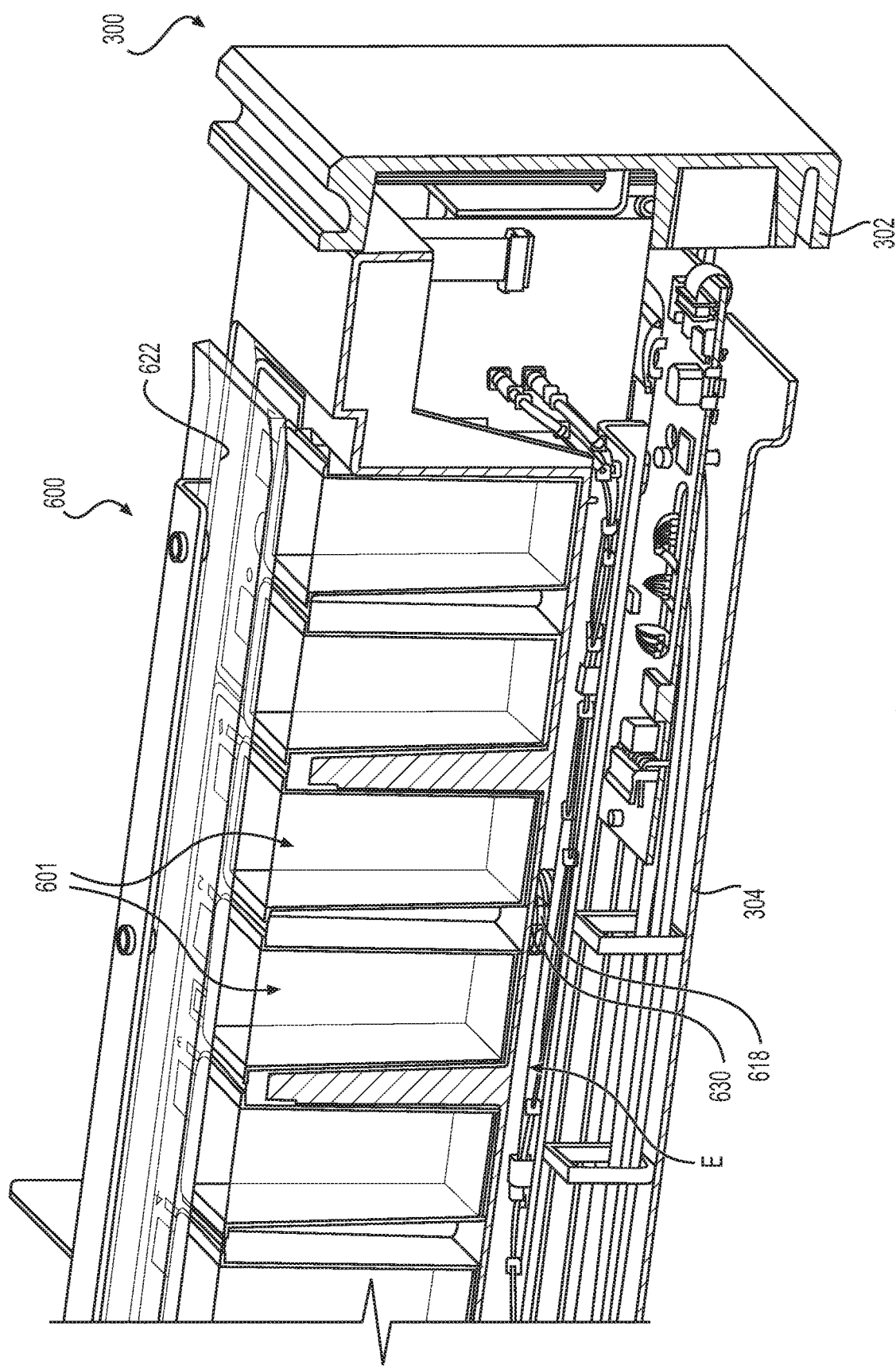
FIG. 20 is a cross-sectional view of an exemplary reagent container-holder coupled to a frame, according to an embodiment.

When reagent container-holder 600 is placed in fluid drawer 300, the metallized portion 616 on bottom wall E of tub portion 610 will be electrically connected to the system ground (e.g., housing of second module 400) and serve as a ground plane. In some embodiments, contact between bottom wall E and the surface of fluid drawer 300 that bottom wall E rests on (which is connected to the system ground) will provide the ground connection to bottom wall E. In some embodiments, springs or other conductive components (such as washers, spacers, conductive foam, conductive sponge, etc.) may be placed between bottom wall E and the mating surface of fluid drawer 300 (for e.g., at the knobs 618, see FIG. 19A) for good electrical connection between bottom wall E and the mating surface. FIG. 20 is a cross-sectional view of reagent container-holder 600 positioned in fluid drawer 300. As illustrated in FIG. 20, in some embodiments, electrically conductive springs 630 may be positioned at knobs 618 (e.g., around knobs 618) for good electrical connection to the system ground.

When reagent container-holder 600 is positioned in fluid drawer 300, a robotic pipettor (e.g., pipettor 200 of FIG. 1A) of second module 400 may pierce through sealing foil 604 of a reconstitution fluid container 602 in receptacle 601 to extract reconstitution fluid from container 602. As described with reference to pipettor 800 of FIG. 16, pipettor 200 may also be configured to measure the fluid level in container 602 by capacitive fluid level sensing. The capacitive fluid level measurements may occur in a manner similar to that described above with respect to pipettor 800. During the capacitive fluid level measurements, the metallized portion 616 on bottom wall E of container-holder 600 that is connected to the system ground serves as the ground plane. Since the ground plane (bottom wall E) is positioned close to the base of the fluid in container 602, the measured capacitance signal or the measured spike will be very sensitive to (and therefore a good indicator of) the fluid level in container 602. Thus, providing a metallized portion 616 proximate bottom wall E (or near the base of container 602) improves the accuracy and sensitivity of fluid level measurement in container 602. Electrically decoupling sealing foil 604 from the ground plane using nonconductive top portion 622 of lid 620 may also assist in identifying entry-related capacitance signals and thereby improve the accuracy of the fluid level measurement as described with reference to FIG. 17.

Thus, grounded metallized portions provided in close proximity to the base of a fluid filled container improves the sensitivity of fluid level measurement using capacitive fluid level measurement. The metallized portion may be grounded by any method known in the art. For example, by connecting the metallized portion to the system ground, to an isolated voltage source, etc. In some embodiments, electrically decoupling the lid of the container from the ground plane using an intervening insulating member assists in eliminating or reducing false signals to improve the accuracy of the fluid level measurement.

Exemplary methods of handling a fluid container used by an instrument will now be described. In some embodiments, frame 302 is moved to the opened position providing access to an operator. At the opened position, the operator can insert containers 502 in receptacles 501 of container-holder 500, and containers 602 in receptacles 601 of container-holder 600. Then the operator can move frame 302 supporting container-holder 500 (and containers 502 supported by holder 500) from the opened position to the closed position, which positions container-holder 500 within system 10.

In some embodiments, container-holder 500 can be locked to frame 302 while frame 302 is moved to the closed position. So container-holder 500 can be unlocked from frame 302. After container-holder 500 is unlocked from frame 302, transporter 700 can move container-holder 500 to different positions within system 10. For example, transporter 700 can move container-holder 500 from the recess 636 on frame 302 along a path to another position within system 10. The travel path of container-holder 500 can include a vertical component. For example, the traveled path can be arcuate. Moving container-holder 500 can include rotating at least one arm 704 coupled to holder support 720 using actuator 702, thereby moving holder support 720 along the traveled path, in some embodiments. In some embodiments, transporter 700 moves container-holder 500 from recess 636 on frame 302, which is positioned within second module 400 of system 10, to position 150 within first module 100.

Again, in some embodiments, second module 400 is configured to perform analyses on samples, and first module 100 is configured to perform analyses on samples different than the analyses performed by second module 400. For example, the analyses performed by first module 100 can include performing nucleic acid amplification reactions that require thermal cycling, such as PCR reactions. And the analyses performed by second module 400 can include nucleic acid amplification reactions that require isothermal conditions for the duration of the nucleic acid amplification reactions, such as TMA reactions, NASBA reactions, and SDA reactions.

In some embodiments, container-holder 500 can be unlocked from frame 302 by moving arm 644 from the locked arm position to the unlocked arm position, as discussed above. Container-holder 500 can be unlocked from frame 302 either after or concurrently with moving frame 302 to the closed position.

In some embodiments, container-holder 500 can be cooperatively engaged with holder support 720 of transporter 700 when frame 302 is at the closed position. Container-holder 500 can cooperatively engage holder support 720 either after or concurrently with moving frame 302 to the closed position.

In some embodiments, after transporter 700 moves container-holder 500 to position 150 in first module 100, a probe tip of a fluid transfer device (similar to pipettor 200 in FIG. 1A) is inserted into fluid container 502 supported by container-holder 500, and then at least a portion of fluid in fluid container 502 is aspirated with the fluid transfer device. After aspiration, the probe tip can be withdrawn from fluid container 502. Top portion 722 of holder support 720 can inhibit upward vertical movement of fluid container 502 relative to container-holder 500, as described above.

Then after all or some of fluid in fluid container 502 is aspirated at position 150 in first module 100, transporter 700 can move container-holder 500 back to frame 302 in second module 400. For example, transporter 700 can reseat container-holder 500 in recess 636 on frame 302 such that protrusions 640A and 640B are received in slots 532A and 532B and that knobs 522A, 522B, 528A, and 528B extend through respective openings 641A, 641B, 642A, and 642B.

Then if fluid containers 502 or fluid containers 602 need to be replaced, frame 302 can be moved, either manually or automatically, from the closed position to the opened position, providing the operator access to both fluid containers 502 and fluid containers 602. The operator can then manually remove used fluid containers 502 in receptacles 501 of container-holder 500 and fluid container 602 in receptacles 501 of container-holder 600. When containers 502 are removed from container-holder 500 when frame is at the opened position, container-holder 500 is locked to frame 302. Container-holder 500 can be locked to frame 302 either before or concurrently with moving frame 302 to the opened position.

In some embodiments, fluid in containers 502 can be aspirated when container-holder 500 is positioned in recess 636 of frame 302, which is at the closed position. In such embodiments, a probe tip of fluid transfer device 200 of second module 400 can be inserted into fluid container 502. Then at least a portion of fluid in fluid container 502 can be aspirated using fluid transfer device 200, and afterwards, the probe tip of the fluid transfer device 200 can be withdrawn from fluid container 502.

Although in some of the above described embodiments container 502 is described as containing an elution buffer, container 502 can contain any desired reagent, including non-elution buffer reagents.

Although specific embodiments are described above, as a person skilled in the art would recognize, many variations of the disclosed embodiments are possible, and therefore, within the scope of this disclosure.

What is claimed is:

1. A holder for supporting one or more containers of fluid, the holder comprising:
    a bottom wall comprising a first electrically nonconductive portion and a first electrically conductive metal coating (i) affixed to an outer surface of the first electrically nonconductive portion, (ii) forming an outer surface of the bottom wall, and (iii) for connection to an electrical ground or voltage source;
    a top surface defining one or more openings;
    one or more receptacles, wherein each receptacle of the one or more receptacles extends from an opening of the one or more openings towards the bottom wall, and wherein each receptacle is configured to receive at least one container of the one or more containers;
    first and second side walls, wherein the one or more receptacles are between the first and second side walls, and wherein at least one of the first and second side walls comprises a second electrically conductive metal coating (i) affixed to an outer surface of a second electrically nonconductive portion of the at least one of the first and second side walls, (ii) forming an outer surface of the at least one of the first and second side walls, (iii) contiguous with the first electrically conductive metal coating of the bottom wall, and (iv) for connection to the electrical ground or voltage source; and
    an RFID tag affixed to an electrically non-conductive surface of the holder.

2. The holder of claim 1, wherein the first electrically nonconductive portion of the bottom wall and the second electrically nonconductive portion of the at least one of the first and second side walls each comprise an electrically non-conductive plastic.

3. The holder of claim 1, wherein the first electrically conductive metal coating of the bottom wall and the second electrically conductive metal coating of the at least one of the first and second side walls are both made of either aluminum or copper.

4. The holder of claim 1, wherein the one or more receptacles include multiple receptacles.

5. The holder of claim 1, wherein the first electrically nonconductive portion of the bottom wall includes an inner surface, and each receptacle of the one or more receptacles extends from one of the one or more openings on the top surface to the inner surface of the bottom wall opposite the outer surface.

6. The holder of claim 1, wherein the second electrically conductive metal coating of the at least one of the first and second side walls covers about 20% to about 30% of a vertical height of the second electrically nonconductive portion of the at least one of the first and second side walls.

7. The holder of claim 1, wherein the second electrically conductive metal coating of the at least one of the first and second side walls covers substantially the entirety of the second electrically nonconductive portion of the at least one of the first and second side walls.

8. The holder of claim 1, wherein the second electrically conductive metal coating of the at least one of the first and second side walls has a thickness between about 0.5 mils and about 2.0 mils.

9. The holder of claim 1, wherein the first electrically conductive metal coating of the bottom wall has a thickness between about 0.5 mils to about 2.0 mils.

10. The holder of claim 1, wherein the first and second electrically nonconductive portions comprise the same material.

11. The holder of claim 1, wherein the first and second electrically conductive metal coatings comprise the same metal.

12. The holder of claim 1, wherein:
    the first electrically conductive metal coating of the bottom wall has a thickness between about 0.5 mils to about 2.0 mils;
    the second electrically conductive metal coating of the at least one of the first and second side walls has a thickness between about 0.5 mils and about 2.0 mils;
    the first and second electrically nonconductive portions comprise the same material; and
    the first and second electrically conductive metal coatings comprise the same metal.

13. The holder of claim 12, wherein the second electrically conductive metal coating of the at least one of the first and second side walls covers about 20% to about 30% of a vertical height of the second electrically nonconductive portion of the at least one of the first and second side walls.

14. The holder of claim 12, wherein the second electrically conductive metal coating of the at least one of the first and second side walls covers substantially the entirety of the second electrically nonconductive portion of the at least one of the first and second side walls.

* * * * *